United States Patent
Wang et al.

(10) Patent No.: US 10,568,984 B2
(45) Date of Patent: Feb. 25, 2020

(54) BIOLOGICAL TISSUE ADHESIVE COMPOSITION AND METHOD OF PREPARATION THEREOF

(71) Applicant: Nanyang Technological University, Singapore (SG)

(72) Inventors: Dongan Wang, Singapore (SG); Changjiang Fan, Singapore (SG)

(73) Assignee: Nanyang Technology University, Singapore (SG)

( * ) Notice: Subject to any disclaimer, the term of this patent is extended or adjusted under 35 U.S.C. 154(b) by 27 days.

(21) Appl. No.: 15/326,420

(22) PCT Filed: Jul. 16, 2015

(86) PCT No.: PCT/SG2015/050217
§ 371 (c)(1),
(2) Date: Jan. 13, 2017

(87) PCT Pub. No.: WO2016/010484
PCT Pub. Date: Jan. 21, 2016

(65) Prior Publication Data
US 2017/0216485 A1 Aug. 3, 2017

(30) Foreign Application Priority Data

Jul. 16, 2014 (SG) .............................. 10201404115P

(51) Int. Cl.
 *A61L 24/10* (2006.01)
 *A61L 24/00* (2006.01)
 *A61L 24/04* (2006.01)
 *A61L 24/02* (2006.01)

(52) U.S. Cl.
 CPC ......... *A61L 24/104* (2013.01); *A61L 24/0031* (2013.01); *A61L 24/02* (2013.01); *A61L 24/043* (2013.01); *A61L 24/10* (2013.01)

(58) Field of Classification Search
 None
 See application file for complete search history.

(56) References Cited

U.S. PATENT DOCUMENTS

2014/0193360 A1  7/2014 Lee et al.

FOREIGN PATENT DOCUMENTS

WO  2013/134269 A2  9/2013
WO  2013/142028 A1  9/2013

OTHER PUBLICATIONS

John D. Ferry, "Mechanical Properties of Substances of High Molecular Weight. IV. Rigidities of Gelatin Gels; Dependence on Concentration, Temperature and Molecular Weight," Journal of the American Chemical Society, vol. 70, No. 6, pp. 2244-2249 (Year: 1948).*
Brennan, "Fibrin Glue," *Blood Reviews* 5:240-244, 1991.
Brubaker et al., "Enzymatically Degradable Mussel-Inspired Adhesive Hydrogel," *Biomacromolecules* 12:4326-4334, 2011.
Brubaker et al., "Biological performance of mussel-inspired adhesive in extrahepatic islet transplantation," *Biomaterials* 31:420-427, 2010.
Choi et al., "Human gelatin tissue-adhesive hydrogels prepared by enzyme-mediated biosynthesis of DOPA and $Fe^{3+}$ ion crosslinking," *Journal of Materials Chemistry B* 2:201-209, 2014.
Chung et al., "Seroma Prevention Using *Mytilus edulis* Protein in a Rat Mastectomy Model," *The Breast Journal* 12(5):442-445, 2006.
Chung et al., "Rapidly Cross-Linkable DOPA Containing Terpolymer Adhesives and PEG-Based Cross-Linkers for Biomedical Applications," *Macromolecules* 45:9666-9673, 2012.
Eroğlu et al., "Reducing seroma formation with fibrin glue in an animal mastectomy model," *European Journal of Surgical Oncology* 22:137-139, 1996.
Hoffmann et al., "Characterisation of a new bioadhesive system based on polysaccharides with the potential to be used as bone glue," *J Mater Med* 20:2001-2009, 2009.
Lee et al., "Thermo-sensitive, injectable, and tissue adhesive sol-gel transition hyaluronic acid/pluronic composite hydrogels prepared from bio-inspired catechol-thiol reaction," *Soft Matter* 6:977-983, 2010.
Lee et al., "A reversible wet/dry adhesive inspired by mussels and geckos," *Nature* 448:338-342, 2007, 6 pages.
Lee et al., "Single-molecule mechanics of mussel adhesion," *PNAS* 103(35):12999-13003, 2006.
Liang et al., "Crosslinking Structures of Gelatin Hydrogels Crosslinked with Genipin or a Water-Soluble Carbodiimide," *Journal of Applied Polymer Science* 91:4017-4026, 2004.

(Continued)

*Primary Examiner* — Dennis J Parad
(74) *Attorney, Agent, or Firm* — Seed IP Law Group LLP

(57) ABSTRACT

A biological tissue adhesive composition is provided. The biological tissue adhesive composition comprises one or more macromolecules grafted with at least one catechol moiety and comprising at least one cross-linkable functional group, a first cross-linker for cross-linking the at least one catechol moiety, wherein the first cross-linker comprises or consists or a multivalent metal ion, and a second cross-linker for covalently cross-linking the at least one cross-linkable functional group, wherein the one or more macromolecules are cross-linked by (a) complex formation between the at least one catechol moiety and the multivalent metal ion, and (b) covalent bonding of the at least one cross-linkable functional group with the second cross-linker. Fabrication method and working principle of a biological tissue adhesive composition are also provided.

18 Claims, 13 Drawing Sheets

(56) References Cited

OTHER PUBLICATIONS

Mehdizadeh et al., "Design Strategies and Applications of Tissue Bioadhesives," *Macromolecular Bioscience* 13:271-288, 2013.

Mehdizadeh et al., "Injectable citrate-based mussel-inspired tissue bioadhesives with high wet strength for sutureless wound closure," *Biomaterials* 33:7972-7983, 2012.

Menyo et al., "Versatile tuning of supramolecular hydrogels through metal complexion of oxidation-resistant catechol-inspired ligands," *Soft Matter* 9:10314-10323, 2013.

Moulay, "Dopa/Catechol-Tethered Polymers: Bioadhesives and Biomimetic Adhesive Materials," *Polymer Reviews* 54(3):436-513, 2014.

Murphy et al., "Adhesive Performance of Biomimetic Adhesive-Coated Biologic Scaffolds," *Biomacromolecules* 11:2976-2984, 2010.

Ninan et al., "Adhesive strength and curing rate of marine mussel protein extracts on porcine small intestinal submucosa," *Acta Biomaterialia* 3:687-694, 2007.

Otani et al., "Hemostatic Capability of rapidly curable glues from gelatin, poly(L-glutamic acid), and carbodiimide," *Biomaterials* 9:2091-2098, 1998.

Peppas et al., "Hydrogels in Biology and Medicine: From Molecular Principles to Bionanotechnology," *Advanced Materials* 18:1345-1360, 2006.

Reece et al., "A prospectus on tissue adhesives," *The American Journal of Surgery* 182:40S-44S, 2001.

Ryan et al., "A Pathophysiologic, Gastroenterologic, and Radiologic Approach to the Management of Gastric Varices," *Gastroenterology* 126:1175-1189, 2004.

Ryu et al., "Catechol-Functionalized Chitosan/Pluronic Hydrogels for Tissue Adhesives and Hemostatic Materials," *Biomacromolecules* 12:2653-2659, 2011.

Sanders et al., "Effect of Fibrinogen and Thrombin Concentrations on Mastectomy Seroma Prevention," *Journal of Surgical Research* 61:65-70, 1996.

Seo et al., "Swelling and Metal-Ion Adsorption Properties of Dopamine-Conjugated Polyaspartate Hydrogel," *J Polym Environ* 23:90-96, 2015.

Sung et al., "Evaluation of gelatin hydrogel crosslinked with various crosslinking agents as bioadhesives: In vitro study," *Journal of Biomedical Materials Research* 46(4):520-530, 1999.

Wang et al., "Co-polypeptides of 3, 4-dihydroxyphenylalanine and L-lysine to mimic marine adhesive protein," *Biomaterials* 28:3456-3468, 2007.

Zeiger et al., "Genetic toxicity and carcinogenicity studies of glutaraldehyde—a review," *Mutation Research* 589:136-151, 2005.

Extended European Search Report, dated Mar. 7, 2018, for European Application No. 15821381.9-1109 / 3169373, 9 pages.

Kim et al., "Super water absorbing hydrogels with good metal ion adsorption" STN-International accession No. 161:567671 (abstract), Oct. 30, 2014, 2 pages.

Xu et al., "Structural effects of catechol-containing polystyrene gels based on a dual cross-linked approach," *Soft Matter* 9:1967-1974, 2013.

\* cited by examiner

BIOLOGICAL TISSUE ADHESIVE COMPOSITION AND METHOD OF PREPARATION THEREOF

CROSS-REFERENCE TO RELATED APPLICATION

This application claims the benefit of priority of Singapore patent application No. 10201404115P filed on 16 Jul. 2014, the content of which is incorporated herein by reference in its entirety for all purposes.

TECHNICAL FIELD

Various embodiments relate to a biological tissue adhesive composition and a method of preparing a biological tissue adhesive composition.

BACKGROUND

Breast cancer accounts for about 23% of all cancers in women, and is the most common malignancy in the world. Mastectomy to remove affected breast tissue by surgery is a frequently adopted treatment option. Seroma formation, which refers to accumulation of fluid in vivo after surgery, is a common complication.

Incidence of seroma formation after mastectomy may reach maximally 53%, and may cause many complications including infection, flap necrosis, and delayed wound healing, which brings huge sufferings to the patients. It is believed that the dead space between the skin and adjacent tissues results in seroma formation.

Conventional methods against seroma formation include tacking down the skin flap and placement of drains at the surgery site. Each of these methods suffers from limitations. For example, the tacking method may be effective to close the auxiliary dead space, but may perform poorly to prevent seepage from the transaction.

Placement of drains presents the route for bacterial invasion due to their invasive nature, and may easily result in deep wound infection. Moreover, use of suction drainage may increase chance of flap necrosis and peripheral nerve damage. Gluing of the skin flap and adjacent tissues together with tissue adhesive, so as to physically close up the auxiliary dead space for seroma formation, is considered an effective strategy to prevent seroma formation.

Currently available tissue adhesives, such as fibrin glue, cyanoacrylate adhesives, or glutaraldehyde-based adhesives, have been successfully used for hemostasis and open/skin wound sealing. There are, however, still no suitable tissue adhesives for large-area in vivo usage such as seroma prevention.

An ideal tissue adhesive for large-area in vivo applications should be (1) safe and non-toxic, (2) rapidly cross-linkable, and (3) possess long-term effectiveness in physiologically wet environments. For instance, as constituents of fibrin glue (fibrinogen and thrombin) are from blood, use of fibrin glue inevitably runs the risk of blood-mediated pathogen transmission. As another example, cyanoacrylate- or glutaraldehyde-based adhesives have exhibited acute and/or chronic toxicity.

Many adhesives, sealants, and haemostats have been developed and approved by US Food and Drug Administration (FDA), as shown in TABLE 1.

TABLE 1

| FDA-approved tissue adhesives, sealants, and haemostats | | | | |
|---|---|---|---|---|
| Adhesives/Sealants | Product Brands (Chemical name) | Indicated Applications | Pros | Cons |
| Fibrin Glue | Tisseel and Evicel (Human pooled plasma fibrinogen and thrombin). Vitagel and Cryoseal system (Autologous plasma fibrinogen and thrombin). | As an adjunct hemostat in surgery. As an adjunct for the closure of colostomies. Vitagel is used as an adjunct hemostat during surgical procedures. Cryoseal system is used as an adjunct hemostat on liver resection. | Fast curing. Biocompatibility. Biodegradability. | Transferring risk of blood-borne disease. Risk of allergic reaction. Risk of infection transmission. Long preparation time. Poor tissue adhesion. Expensive. Ancillary equipment required. |
| Albumin and Glutaraldehyde | BioGlue (Bovine serum albumin and 10% glutaraldehyde) | As an adjunct hemostat for standard methods (such as suture and staple) in open surgical to repair large vessels. | Fast crosslinking. Good adhesion to tissue. | Toxicity of glutaraldehyde. |
| Cyanoacrylates | Dermabond (2-Octyl cyanoacrylate) Indermil (n-Butyl-2-cyanoacrylate) Histoacryl and | Closure of topical skin. Conjunction with but no in deep dermal stitches. Closure of | Fast polymerization. Strong adhesion Relatively inexpensive. | Exothermic crosslinking. Prolonged degradation. Toxicity of degradation products. |

TABLE 1-continued

FDA-approved tissue adhesives, sealants, and haemostats

| Adhesives/Sealants | Product Brands (Chemical name) | Indicated Applications | Pros | Cons |
|---|---|---|---|---|
|  | Histoacryl Blue (n-Butyl-2-cyanoacrylate) | skin wounds. Skin closure in endoscopic incisions. |  | Limited to topical uses. |
| Poly(ethylene glycol) (PEG) based sealants | Coseal (four-armed PEGs, capped With glutaryl-succinimidyl ester or the other with thiols, and dilute solution of hydrogen chloride and sodium phosphate-sodium carbonate) Duraseal (PEG ester powder and trilysine amine solution with FD&C blue No. 1 dye). | Sealing suture lines and vascular graft. Sealing of cerebrospinal fluid. | Rapid gel formation. Biocompatibility. Fast hemostasis. | Risk of swelling. Possible allergic reaction. Relatively expensive. |

All the substances listed are commercially available, and have been used in surgeries. None of the products is, however, competent for large-area in vivo applications such as seroma prevention, although fibrin glue and Bioglue were once considered promising candidates.

Fibrin glue contains fibrinogen and thrombin, both of which come from blood and bears risk of infection contamination. Due to the weak bonding strength and fast degradation of fibrin glue, its current applications are to control bleeding, during or after surgeries. Bioglue is composed of bovine serum albumin and 10% glutaraldehyde. Recent studies have shown that use of glutaraldehyde in vivo is associated with some diseases such as cancer and leukemia.

Further examples of adhesives, sealants, and haemostats are provided in TABLE 2, where limitations, such as complicated synthesis and long cure time, are present.

TABLE 2

Further examples of adhesives, sealants, and haemostats

| Chemical component | Indicated Applications | Adhesion and cure time | Pros | Cons |
|---|---|---|---|---|
| 3,4-dihydroxyphenylalanine and L-lysine | Bond of porcine skin and porcine bone | 155 kPa and 12 hours | Strong adhesion Biocompatibility | Long cure time Complicated synthesis Need high temperature, vacuum and organic solvent Expensive |
| Four-arm poly(ethylene glycol), 3,4-dihydroxyhydrocinnamic acid and sodium periodate | Immobilize transplanted islet | No reported adhesion and 20-30 seconds | Fast crosslinking | Complicated synthesis |
| Citric acid, PEG, and dopamine | Wounds closure | 123 kPa and two hours | Biocompatibility | Nondegradable Complicated synthesis Need high temperature and vacuum Relatively expensive |
| Extracted adhesive protein from marine mussels (*Mytilus edulis*) and metal ions $V^{5+}$, $Fe^{3+}$ and $Cr^{6+}$ | No reported application | 57-462 kPa and several seconds | Fast crosslinking Biocompatibility | Expensive |

TABLE 2-continued

Further examples of adhesives, sealants, and haemostats

| Chemical component | Indicated Applications | Adhesion and cure time | Pros | Cons |
| --- | --- | --- | --- | --- |
| Peptide Fmoc-Ala-Ala-OH, branched poly(ethylene glycol) (PEG), and sodium periodate | Wound closure | 30.4 kPa and two hours | Fast crosslinking | Complicated synthesis Need organic solvent Relatively expensive |
| Polyethylene glycol (PEG), polycaprolactone (PCL), N—Boc-Gly-OH, 3,4-dihydroxyhydrocinnamic acid, and sodium periodate | Hernia repair | 168-357 kPa and two hours | Strong adhesion | Complicated synthesis Need organic solvent Relatively expensive |
| Hyaluronic acid, dopamine, and thiolated Pluronic F127 copolymer | Drug and cell delivery | 7.18 kPa and no reported cure time | Biocompatibility | Complicated synthesis Expensive |
| Gelatin extracted from human adipose tissue, tyrosinase, and $FeCl_3$ solution | Hemostat of hemorrhaging liver | No reported adhesion and cure in seconds | Biocompatibility Fast gelation | Complicated preparation instable in vivo Expensive |
| Chitosan, thiolated Pluronic F-127, and hydrocaffeic acid | Hemostat of hemorrhaging liver | 20.8 kPa and 48 hours | Biocompatibility | Complicated synthesis Expensive |
| Thiolated 3-armed poly(ethylene glycol), 3,4-dihydroxy-L-phenylalanine, N-hydroxysuccinimide ester, and acrylic acid | Skin closure | About 11 kPa and 10 minutes | Fast gelation | Nondegradable Complicated synthesis |

In view of the above, there exists a need for an improved biological tissue adhesive that overcomes or at least alleviates one or more of the above-mentioned problems.

SUMMARY

In a first aspect, a biological tissue adhesive composition is provided. The biological tissue adhesive composition comprises
  (i) a gluing macromer comprising one or more macromolecules grafted with at least one catechol moiety and comprising at least one cross-linkable functional group,
  (ii) a first cross-linker for cross-linking the at least one catechol moiety, wherein the first cross-linker comprises or consists of a multivalent metal ion, and
  (iii) a second cross-linker for covalently cross-linking the at least one cross-linkable functional group,
wherein the one or more macromolecules are cross-linked by (a) complex formation between the at least one catechol moiety and the multivalent metal ion, and (b) covalent bonding of the at least one cross-linkable functional group with the second cross-linker.

In a second aspect, a method of preparing a biological tissue adhesive composition is provided. The method comprises
  a) providing a mixture of a gluing macromer comprising one or more macromolecules grafted with at least one catechol moiety and comprising at least one cross-linkable functional group, and a second cross-linker for covalently cross-linking the at least one cross-linkable functional group; and
  b) adding a first cross-linker for cross-linking the at least one catechol moiety, wherein the first cross-linker comprises or consists of a multivalent metal ion, to the mixture so as to cross-link the one or more macromolecules by complex formation between the at least one catechol moiety and the multivalent metal ion.

In a third aspect, a biological tissue adhesive composition prepared by a method according to the second aspect is provided.

In a fourth aspect, a kit for adhering biological tissues is provided. The kit comprises
  a) a gluing macromer comprising one or more macromolecules grafted with at least one catechol moiety and comprising at least one cross-linkable functional group;
  b) a first cross-linker for cross-linking the at least one catechol moiety, wherein the first cross-linker comprises or consists of a multivalent metal ion; and
  c) a second cross-linker for covalently cross-linking the at least one cross-linkable functional group.

In a fifth aspect, a method of adhering biological tissues is provided. The method comprises
  a) applying a mixture of a gluing macromer comprising one or more macromolecules grafted with at least one catechol moiety and comprising at least one cross-linkable functional group, and a second cross-linker for covalently cross-linking the at least one cross-linkable functional group on a first biological tissue to form a coating;
  b) adding a first cross-linker for cross-linking the at least one catechol moiety, the first cross-linker comprising or consisting of a multivalent metal ion, to the coating;

c) contacting a second biological tissue with the resultant coating; and d) applying pressure to one or both the first biological tissue and the second biological tissue to adhere the first biological tissue to the second biological tissue.

In a sixth aspect, use of a biological tissue adhesive composition according to the first aspect or prepared by a method according to the second aspect as a tissue adhesive and sealant for medical and veterinary applications, in seroma prevention, wound closure, supplementing or replacing sutures or staples in internal surgical procedures, intestinal anastomosis, vascular anastomosis, tissue repair, ophthalmic procedures, drug delivery, prevention of post-surgical adhesions, and/or tissue implantation is provided.

BRIEF DESCRIPTION OF THE DRAWINGS

The invention will be better understood with reference to the detailed description when considered in conjunction with the non-limiting examples and the accompanying drawings, in which.

DETAILED DESCRIPTION

Figure 1:
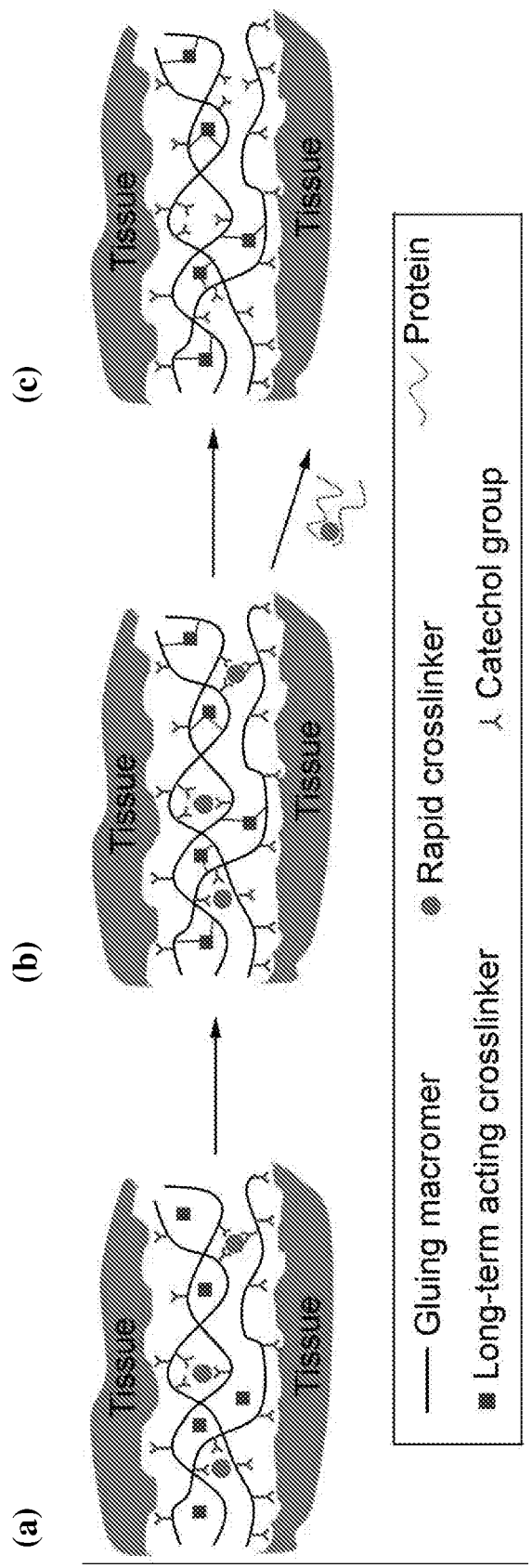
FIG. 1 is a schematic diagram depicting working principle of the novel tissue adhesives fabricated with the concept of double-cross-linking, where (a), the catechol-grafted gluing macromers are rapidly cross-linked with the rapid cross-linker (first cross-linker) by ion-catechol complexation, at the same time, catechol groups bind to tissue surfaces through non-covalent interactions, hence the both tissues are glued together instantaneously; (b) after a period of time (hours), the gluing macromers are also cross-linked with the long-term acting cross-linker (second cross-linker); and (c) although the rapid cross-linkers gradually lose by complexation of proteins in vivo, the tissue adhesive still works due to the covalent cross-linking of gluing macromers formed with long-term acting cross-linkers.

Various embodiments refer in a first aspect to a biological tissue adhesive composition. The biological tissue adhesive composition disclosed herein has been constructed using a complexation-covalent double-crosslinking principle. A gluing macromer comprising one or more macromolecules grafted with at least one catechol moiety and comprising at least one cross-linkable functional group may be rapidly cross-linked with a first cross-linker comprising or consisting of a multivalent metal ion by metal ion-catechol complexation, with subsequent covalent bonding of the cross-linkable functional group with a second cross-linker, which may be a long-acting cross-linking agent. The rapid cross-linking by metal ion-catechol complexation may provide initial stability of the biological tissue adhesive composition, as well as to allow time for formation of a more stable covalent bonding between the cross-linkable functional group and the second cross-linker. In so doing, long-term effectiveness of the biological tissue adhesive composition under physiology conditions may be obtained. Further, use of coupling chemistry to form catechol-grafted gluing macromers such as gelatine-dopamine conjugates disclosed herein allow grafting degree of catechol groups to be controlled within a wide range.

Advantageously, preparation of the biological tissue adhesive composition disclosed herein is inexpensive, as raw materials such as gelatin and chitosan are cheap and in abundance. Further, catechol-grafted gluing macromers may be achieved in a one-step reaction without requiring special conditions such as high temperature, high vacuum, and/or high pressure, or special equipment. Ease of use of the biological tissue adhesive composition renders its feasibility for clinical applications. The biological tissue adhesive composition disclosed herein also exhibits relatively high adhesive force, and is cytocompatible as demonstrated herein by results from in vitro experiments.

With the above in mind, the term "biological tissue adhesive composition" as used herein refers to a formulation that may be used to join or to bond biological tissues together. The term "biological tissue" refers to a structure formed by related cells joined together, wherein the cells work together with intercellular substances to accomplish specific functions and/or to form one of the structural materials of a human, animal, plant, bacterial, fungal or viral structure, including connective, epithelium, muscle and nerve tissues. Examples of biological tissue include, but are not limited to, tissues of digestive organs, blood vessels, the heart, the lungs, the urethra, the esophagus, bladder tissue, bone tissue, brain tissue, breast tissue, and diaphragm tissue.

The biological tissue adhesive composition comprises a gluing macromer comprising one or more macromolecules grafted with at least one catechol moiety and comprising at least one cross-linkable functional group. The term "macromolecules", otherwise termed herein as "polymers" or "macromers", refers to any large organic molecule composed of multiple small structural units linked together. The one or more macromolecules may be a natural macromolecule and/or a synthetic macromolecule, meaning that it may be naturally-occurring or artificially created such as via chemical synthesis.

Naturally-occurring macromolecules refer to polymers or macromers that may be found in nature. Examples of naturally-occurring macromolecules include, but are not limited to, polysaccharides, glycosaminoglycans, proteins, and mixtures thereof.

Polysaccharides are carbohydrates which may be hydrolyzed to two or more monosaccharide molecules. They may contain a backbone of repeating carbohydrate i.e. sugar unit. Examples of polysaccharides include, but are not limited to, alginate, agarose, chitosan, dextran, starch, and gellan gum.

Glycosaminoglycans are polysaccharides containing amino sugars as a component.

Amino acids are molecules containing at least one carboxyl group (—COOH) and one amine (—NH$_2$) group. A side chain is present on the amino acid molecule, which can affect properties such as polarity and acid-base properties of the amino acid. The side chain may vary in size from a hydrogen atom in glycine, to a phenyl group in phenylalanine. Further examples of amino acids include aspartic acid, glutamic acid, arginine, lysine, asparagine, glutamine, alanine, tryptophan as well as any non-standard amino acid, such as selenocysteine, lanthionine, 2-aminoisobutyric acid, dehydroalanine or gamma-aminobutyric acid; or amino acid derivatives, such as 5-hydroxytryptophan or L-dihydroxyphenylalanine. Therefore, a protein molecule is made from a long chain of these amino acids, each linked to its neighbor through a covalent peptide (—CONH—) bond.

Examples of glycosaminoglycans include, but are not limited to, hyaluronic acid, chondroitin sulfate, dermatin sulfate, keratin sulfate, dextran sulfate, heparin sulfate, heparin, glucuronic acid, iduronic acid, galactose, galactosamine, and glucosamine.

The term "polypeptide" as used herein refers generally to a single chain amino acid polymer of more than 100 amino acid monomers. Peptides refer generally to amino acid dimers (dipeptides), oligomers (oligopeptides) of up to about 25 to 50 amino acids, and short polymers of about 2 to 100 amino acids in length. The term "protein" as used herein refers generally to a 3D-structure of one or more polypeptide chains that may be non-covalently or covalently (via disulfide bridges) be associated with each other. Examples of proteins include, but are not limited to, collagen, keratin, elastin, sklerotin, fibroin, enzyme, hemoglobin, serum albumin antibodies, thrombin estrogen, adrenalin, insulin, growth hormone, steroid hormone, and thyroid hormone.

In various embodiments, the one or more macromolecules comprises or consists of a natural macromer.

The macromolecule may alternatively be artificially created. Examples of artificially created macromolecules include, but are not limited to, polymers and oligomers of glycolide, lactide, polylactic acid, polyesters of α-hydroxy acids, including lactic acid and glycolic acid, such as the poly(α-hydroxy) acids including polyglycolic acid, poly-DL-lactic, poly-L-lactic acid, and terpolymers of DL-lactide and glycolide, ε-caprolactone and ε-caprolactone copolymerized with polyesters, polylactones and polycaprolactones including poly(ε-caprolactone), poly(δ-valerolactone) and poly (γ-butyrolactone); polyanhydrides, polyorthoesters, other hydroxy acids, polydioxanone, collagen-hydroxyethylmethacrylate (HEMA), poly(hydroxylethyl methacrylate) (PHEMA), and other biologically degradable polymers that are non-toxic or are present as metabolites in the body. The above listed examples of artificially created macromolecules are also biodegradable.

In various embodiments, the one or more macromolecules is selected from the group consisting of an amino group functionalized polysaccharide, a polyamino acid, and combinations thereof.

In some embodiments, the one or more macromolecules is selected from the group consisting of gelatin, bovine serum albumin (BSA), chitosan, polyethylenimine, hyaluronan, dextran, poly(asparagic acid), poly(glutamic acid), and combinations thereof.

In specific embodiments, the one or more macromolecules comprises or consists of gelatin. The term "gelatin" as used herein refers to protein substances derived from collagen. In the context of the present invention, "gelatin" also refers to equivalent substances such as synthetic analogues of gelatin. Generally, gelatin may be classified as alkaline gelatin, acidic gelatin, or enzymatic gelatin. Alkaline gelatin may be obtained from the treatment of collagen with a base such as sodium hydroxide or calcium hydroxide. Acidic gelatin may be obtained from the treatment of collagen with an acid such as hydrochloric acid. Enzymatic gelatin may be obtained from the treatment of collagen with an enzyme such as hydrolase. As gelatin may be a form of hydrogel, factors that affect degradation behavior of hydrogels as mentioned herein may also apply to gelatin.

The one or more macromolecules are grafted with at least one catechol moiety and comprises at least one cross-linkable functional group. Advantageously, the macromolecule does not contain toxic components such as an aldehyde group and/or a cyan group which are present in state of the art biological tissue adhesives.

Catechol refers to the ortho isomer of the three isomeric benzenediols, and has the following structure

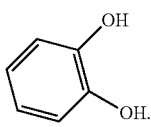

Natural sources of macromolecules containing catechol groups include protein glue secreted by marine mussels. Advantageously, the protein glue is biocompatible and possesses excellent wet adhesion ability. Catechol groups are able to interact with almost all kinds of surfaces. In particular, upon oxidation of catechol groups into quinones, the protein glue possesses strong adhesion to biological surfaces. Furthermore, catechol groups are capable of rapid complex formation with multivalent metal ions such as $Cu^{2+}$, $Zn^{2+}$, $Al^{3+}$, and $Fe^{3+}$, to result in rapid cross-linking.

In various embodiments, the one or more macromolecules grafted with at least one catechol moiety is obtainable by reacting the one or more macromolecules with a catechol-containing compound selected from the group consisting of dopamine, hydrocaffeic acid, dihydroxyphenylalanine, 3,4-dihydroxylhydrocinnamic acid, and combinations thereof.

In some embodiments, the catechol-containing compound is dopamine. Dopamine refers to a catecholamine neurotransmitter or hormone which is typically of the following formula:

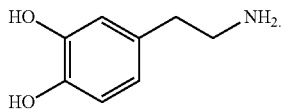

The one or more macromolecules grafted with at least one catechol moiety may otherwise be termed as a conjugate. As used herein, the term "conjugate" refers to a molecule comprised of two or more moieties bound together, optionally through a linking group, to form a single covalent structure. For example, binding between the moieties may be made by a direct chemical bond, such as in the case of gelatin-dopamine conjugates, where linking groups are not used. The dopamine is directly grafted to gelatin by conjugation reaction between the carboxyl group of gelatin and amino group of dopamine.

For example, the gelatin-dopamine conjugate may be formed by coupling the amine group of dopamine and the carboxyl groups of gelatin using standard 1-ethyl-3-(-3-dimethylaminopropyl) carbodiimide hydrochloride/N-hydroxysuccinimide (EDC/NHS) chemistry known to a person skilled in the art. Advantageously, a wide range in grafting degree of the catechol groups may be obtained by controlling the coupling chemistry.

Other examples of conjugates may include, but are not limited to, a bovine serum albumin (BSA)-dopamine conjugate, a chitosan-3,4-dihydroxyhydrocinnamic acid conjugate, a gelatin-3,4-dihydroxyhydrocinnamic acid conjugate, and combinations thereof.

Content of gelatin in the biological tissue adhesive composition may be determined by Arnow's method as known to a person skilled in the art. In various embodiments, amount of gelatin in the biological tissue adhesive composition may be in the range of about 80 wt % to about 99.9 wt %, such as about 82 wt % to about 99.9 wt %, about 88 wt % to about 99.9 wt %, about 92 wt % to about 99.9 wt %, about 80 wt % to about 95 wt %, about 80 wt % to about 92 wt %, about 80 wt % to about 90 wt %, about 80 wt % to about 85 wt %, about 85 wt % to about 95 wt %, or about 83 wt % to about 93 wt %.

As mentioned above, the catechol moiety in the gluing macromer may undergo rapid cross-linking with the multivalent metal ion present in the first cross-linker, such as by metal ion-catechol complex formation. At the same time, the catechol moiety may form moisture resistant bonds with surface of biological tissue surfaces. Amount of catechol moiety in the one or more macromolecules may be in the range of about 0.1% to about 20% (w/w). For example, amount of catechol moiety in the one or more macromolecules may be in the range of about 1% to about 20% (w/w), about 5% to about 20% (w/w), about 10% to about 20% (w/w), about 15% to about 20% (w/w), about 0.1% to about 15% (w/w), about 0.1% to about 10% (w/w), about 0.1% to about 5% (w/w), about 5% to about 15% (w/w), or about 8% to about 18% (w/w).

The macromolecules may have a number average molecular weight greater than 10000 g/mol. The number average molecular weight may be obtained by dividing the weight of a sample by the number of molecules of which it is composed. For example, the macromolecules may have a number average molecular weight greater than about 15000 g/mol, about 30000 g/mol, about 50000 g/mol, about 80000 g/mol, or about 100000 g/mol, such as a value in the range of about 10000 g/mol to about 100000 g/mol, about 10000 g/mol to about 80000 g/mol, about 10000 g/mol to about 50000 g/mol, about 10000 g/mol to about 30000 g/mol, about 20000 g/mol to about 80000 g/mol, about 30000 g/mol to about 60000 g/mol, or about 20000 g/mol to about 50000 g/mol.

The one or more macromolecules are cross-linked by (a) complex formation between the at least one catechol moiety and a multivalent metal ion present in the first cross-linker, and (b) covalent bonding of the at least one cross-linkable functional group with the second cross-linker.

As used herein, the term "cross-link" refers to formation of a bond or interconnection between macromolecules. Examples of cross-linking include physically cross-linking and chemical cross-linking.

Physically cross-linking may, for example, take place via complexation, hydrogen bonding, desolvation, van der Waals interactions, or hydrophobic interaction. Chemical cross-linking, on the other hand, refers to an interconnection between polymer chains via chemical bonding, such as, but not limited to, covalent bonding, ionic bonding, or affinity interactions (e.g. ligand/receptor interactions, antibody/antigen interactions, etc.).

In various embodiments, the one or more macromolecules are first cross-linked by complex formation between the at least one catechol moiety and a multivalent metal ion present in the first cross-linker. The first cross-linker for cross-linking the at least one catechol moiety may comprise or consist of a multivalent metal ion. The term "multivalent metal ion" as used herein refers to a metal ion having a valency of at least two. For example, the multivalent metal ion may be a divalent metal ion such as $Cu^{2+}$ or $Zn^{2+}$, or a trivalent metal ion such as $Al^{3+}$, $Fe^{3+}$, or $Cr^{3+}$. Accordingly, the first cross-linker may be an aqueous solution containing a metal salt, such as $FeCl_3$, $CuCl_2$, $CuSO_4$, $Zn(NO_3)_2$, $ZnSO_4$, to name only a few.

In various embodiments, the multivalent metal ion is a transition metal ion. Examples of transition metal include, but are not limited to, scandium (Sc), titanium (Ti), vanadium (V), chromium (Cr), manganese (Mn), iron (Fe), cobalt (Co), nickel (Ni), copper (Cu), zinc (Zn), and alloys thereof.

In some embodiments, the multivalent metal ion is selected from the group consisting of $Cu^{2+}$, $Zn^{2+}$, $Al^{3+}$, $Fe^{3+}$, $Cr^{3+}$, and combinations thereof. In specific embodiments, the multivalent metal ion comprises or consists of $Fe^{3+}$.

Figure 3:
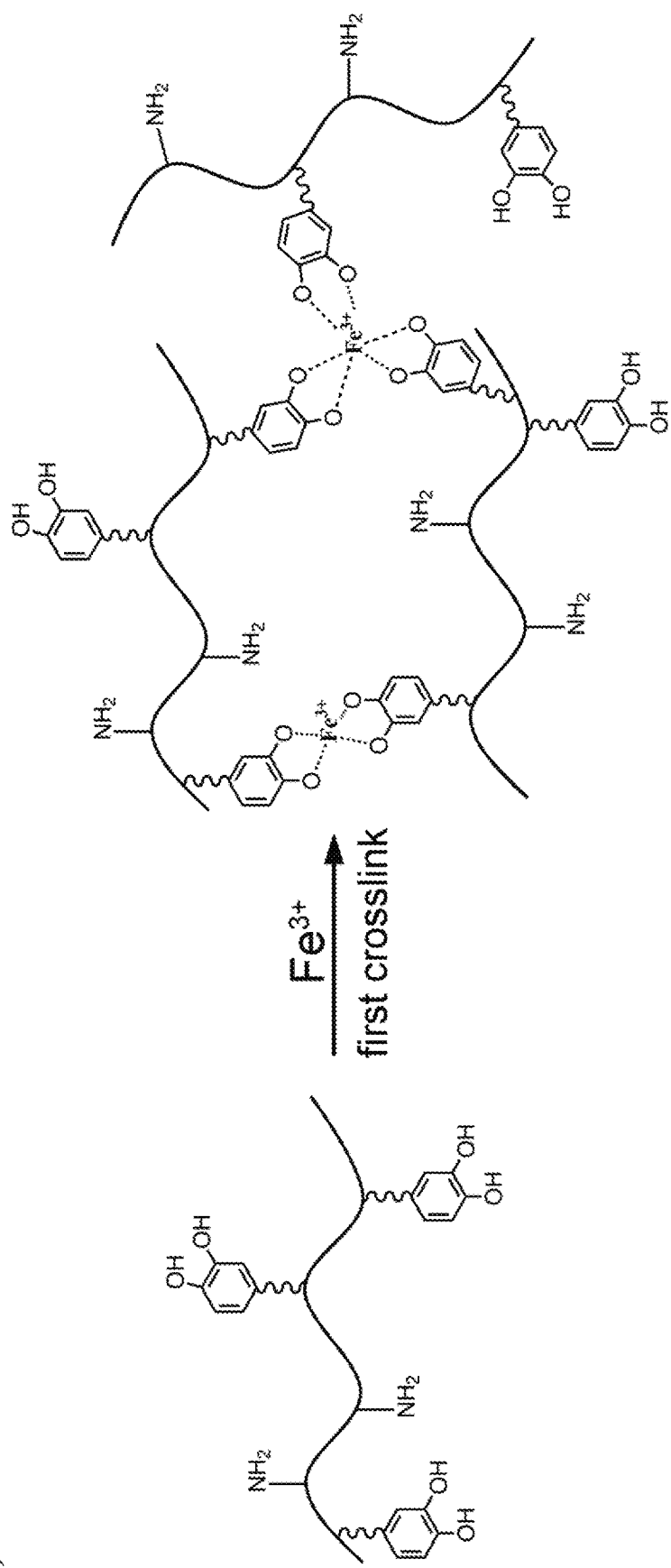
FIG. 3 is a schematic representation of (a) first crosslink, and (b) second crosslink of typical gelatin-dopamine gluing macromers in formation of the tissue adhesive.
Figure 3:
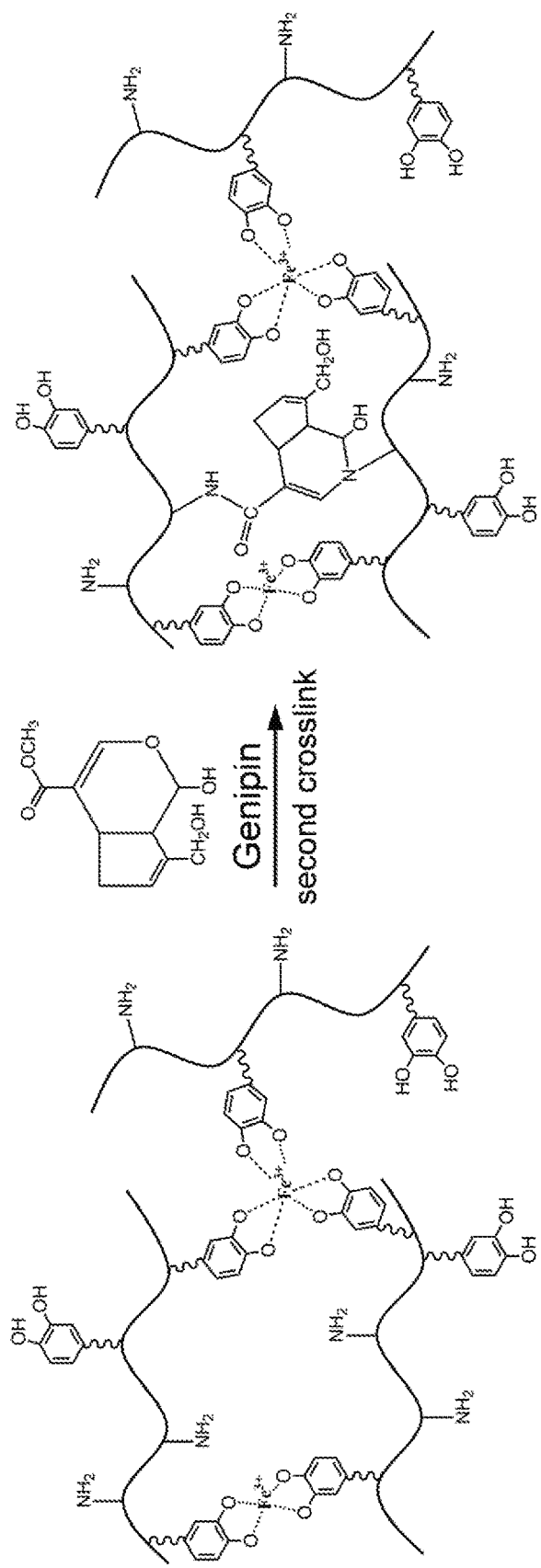

In various embodiments, a complex is formed between the at least one catechol moiety of the macromolecules and the multivalent metal ion. As mentioned above, complex formation between the at least one catechol moiety and the multivalent metal ion may take place rapidly to provide initial stability of the biological tissue adhesive composition. In so doing, this allows formation of more stable covalent bonds between the cross-linkable functional group present in the macromolecule and the second cross-linker. Formation of the complex may result in cross-linking of the macromolecules via the multivalent metal ions to form a three-dimensional network. In various embodiments, the metal ion-catechol complexes are formed by coordination complexation, such as that illustrated in FIG. 3(a) for the first cross-link.

In addition to the above, the one or more macromolecules are also cross-linked by covalent bonding of the at least one cross-linkable functional group with the second cross-linker. The at least one cross-linkable functional group may be a moiety that is able to chemically react with the second cross-linker to form covalent bonds. Formation of the covalent bonds between the at least one cross-linkable functional group and the second cross-linker may take place after complex formation between the at least one catechol moiety grafted on the one or more macromolecules and the multivalent metal ion present in the first cross-linker The second cross-linker for covalently cross-linking the at least one cross-linkable functional group may comprise a compound that is able to react slowly with the one or more macromolecules. Choice of suitable second cross-linker may depend on on the cross-linkable functional groups present on the macromolecules. For example, genipin and polygenipin may only act on amino groups. In such embodiments, the at least one cross-linkable group may comprise or consist of an amino group.

In various embodiments, the at least one cross-linkable functional group is a nucleophilic functional group. For example, the at least one cross-linkable functional group may be selected from the group consisting of an amino group, a thiol group, and combinations thereof. For these cross-linkable functional groups, the second cross-linker may be a macromolecule comprising at least one α,β-unsaturated carbonyl group or α, β-unsaturated sulfonyl group. Examples of suitable second cross-linkers include gelatin-acrylate, hyaluronan-acrylate, poly(ethylene glycol)-acrylate, and/or poly(ethylene glycol) vinylsulfone.

In various embodiments, the second cross-linker comprises or consists of genipin. Genipin is derived from the fruit of gardenia jasminoides, which is biocompatible. It has the following general formula

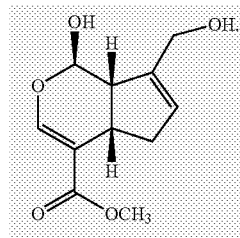

Genipin is able to crosslink macromolecules containing primary amine groups by covalent bonding between itself and the macromolecules. In specific embodiments, the second cross-linker is selected from the group consisting of genipin, polygenipin, genipin-grafted molecule, and combinations thereof.

Time required for covalent bonding of the at least one cross-linkable functional group with the second cross-linker may vary depending on the cross-linkable functional group present and/or second cross-linker used. For example, cross-linking of gelatin-dopamine conjugate with genipin may take place for a time period of about 2 hours.

Various embodiments refer in a second aspect to a method of preparing a biological tissue adhesive composition. The method comprises providing a mixture of a gluing macromer comprising one or more macromolecules grafted with at least one catechol moiety and comprising at least one cross-linkable functional group, and a second cross-linker for covalently cross-linking the at least one cross-linkable functional group.

In various embodiments, providing the mixture comprises dissolving a solid admixture comprising the one or more macromolecules and the second cross-linker in an aqueous solution. In some embodiments, providing the mixture comprises adding an aqueous solution comprising the second cross-linker to an aqueous solution comprising the one or more macromolecules. Examples of macromolecules and second cross-linker have already been discussed above. As also mentioned above, the macromolecule does not contain toxic components such as an aldehyde group and/or a cyan group.

Concentration of macromolecules in the mixture may be in the range of about 10% w/v to about 50% w/v. For example, concentration of macromolecules in the mixture may be in the range of about 15% w/v to about 50% w/v, about 20% w/v to about 50% w/v, about 25% w/v to about 50% w/v, about 30% w/v to about 50% w/v, about 35% w/v to about 50% w/v, about 10% w/v to about 45% w/v, about 10% w/v to about 40% w/v, about 10% w/v to about 35% w/v, about 10% w/v to about 30% w/v, about 20% w/v to about 40% w/v, or about 15% w/v to about 35% w/v.

Concentration of second cross-linker in the mixture may be in the range of about 2 mM to about 40 mM, such as about 10 mM to about 40 mM, about 15 mM to about 40 mM, about 20 mM to about 40 mM, about 25 mM to about 40 mM, about 30 mM to about 40 mM, about 2 mM to about 30 mM, about 2 mM to about 25 mM, about 2 mM to about 20 mM, about 10 mM to about 30 mM, or about 15 mM to about 35 mM.

The method includes adding a first cross-linker for cross-linking the at least one catechol moiety, wherein the first cross-linker comprises or consists of a multivalent metal ion, to the mixture, so as to cross-link the one or more macromolecules by complex formation between the at least one catechol moiety and the multivalent metal ion.

Examples of first cross-linker and multivalent metal ion have already been discussed above. For example, the multivalent metal ion may be a transition metal ion. In various embodiments, the multivalent metal ion is selected from the group consisting of $Cu^{2+}$, $Zn^{2+}$, $Al^{3+}$, $Fe^{3+}$, $Cr^{3+}$, and combinations thereof. In specific embodiments, the multivalent metal ion comprises or consists of $Fe^{3+}$.

Concentration of multivalent metal ion in the biological tissue adhesive composition may be in the range of about 5 mM to about 50 mM. For example, concentration of multivalent metal ion in the biological tissue adhesive composition may be in the range of about 10 mM to about 50 mM, about 15 mM to about 50 mM, about 25 mM to about 50 mM, about 35 mM to about 50 mM, about 5 mM to about 40 mM, about 5 mM to about 30 mM, about 5 mM to about 20 mM, about 15 mM to about 30 mM, or about 20 mM to about 40 mM.

In some embodiments, the mixture comprising one or more macromolecules grafted with at least one catechol moiety and comprising at least one cross-linkable functional group, and a second cross-linker for covalently cross-linking the at least one cross-linkable functional group may be provided by applying the mixture on a biological tissue to form a coating. The first cross-linker comprising the multivalent metal ion may be added to the mixture by dispensing a solution comprising the multivalent metal ion in droplet form on the coating. Other suitable methods to dispense the first cross-linker such as spray coating may alternatively be used.

Various embodiments refer in a third aspect to a biological tissue adhesive prepared by a method according to the second aspect.

Various embodiments refer in a further aspect to a kit for adhering biological tissues. The kit includes a gluing macromer comprising one or more macromolecules grafted with at least one catechol moiety and comprising at least one cross-linkable functional group, a first cross-linker for cross-linking the at least one catechol moiety, wherein the first cross-linker comprises or consists of a multivalent metal ion, and a second cross-linker for covalently cross-linking the at least one cross-linkable functional group.

As mentioned above, a user may apply the gluing macromer comprising the one or more macromolecules and the second cross-linker on a biological tissue to form a coating, with subsequent addition of the first cross-linker to the mixture. In so doing, a biological tissue adhesive composition according to embodiments disclosed herein may be formed.

In alternative embodiments, the one or more macromolecules and the second cross-linker may be present as a mixture in the kit.

Various embodiments refer in a fifth aspect to a method of adhering biological tissues. The method comprises applying a mixture of a gluing macromer comprising one or more macromolecules grafted with at least one catechol moiety and comprising at least one cross-linkable functional group, and a second cross-linker for covalently cross-linking the at least one cross-linkable functional group on a first biological tissue to form a coating. This is followed by adding a first cross-linker comprising or consisting of a multivalent metal ion to the coating. In so doing, a biological tissue adhesive composition is obtained. A second biological tissue is brought into contact with the resultant coating, and pressure is applied to one or both the first biological tissue and the second biological tissue to adhere the first biological tissue to the second biological tissue.

In some embodiments, instead of adding the first cross-linker comprising a multivalent metal ion to the coating, the first cross-linker comprising multivalent metal ion may be added to the second biological tissue. The second biological tissue may be brought into contact with the first biological tissue such that the first cross-linker containing multivalent metal ion is in contact with the coating to form a biological tissue adhesive. Pressure may be applied to one or both the first biological tissue and the second biological tissue to adhere the first biological tissue to the second biological tissue.

Various embodiments refer in a further aspect to use of a biological tissue adhesive composition according to the first aspect, or prepared by a method according to the second aspect as a tissue adhesive and sealant for medical and veterinary applications, in seroma prevention, wound closure, supplementing or replacing sutures or staples in internal surgical procedures, intestinal anastomosis, vascular anastomosis, tissue repair, ophthalmic procedures, drug delivery, prevention of post-surgical adhesions, and/or tissue implantation.

For example, the tissue adhesive composition may be used to glue tissue in tissue implantation such as cartilage glue, bone glue, (cardiac) muscle glue, and fat glue.

Hereinafter, the present invention will be described more fully with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, lengths and sizes of layers and regions may be exaggerated for clarity.

As used herein, the term "and/or" includes any and all combinations of one or more of the associated listed items. The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are in terms of Markush groups, those skilled in the art will recognize that the invention is also thereby described in terms of any individual member or subgroup of members of the Markush group.

EXPERIMENTAL SECTION

An ideal tissue adhesive for large-area in vivo applications should be (1) safe and nontoxic, (2) rapidly cross-linkable, (3) long-term effective, and (4) biodegradability in physiological environments (where are full of tissue fluid).

In various embodiments disclosed herein, a novel aldehyde-free double cross-linked biological tissue adhesive composition is designed and developed by constituting (1) gelatin-dopamine conjugates (containing catechol groups)—as a typical gluing macromer, (2) $Fe^{3+}$—as a typical rapid cross-linker; and, (3) genipin—as a typical long-acting cross-linker.

The gelatin-dopamine gluing macromer may be rapidly cross-linked with $Fe^{3+}$ by catechol-$Fe^{3+}$ complexation; though such single cross-linking alone may not be stable under physiological condition with presence of serum proteins. The gelatin-dopamine gluing macromer may also be covalently cross-linked by genipin alone, whereas this single-cross-linking process may take too long (in the order of hours). Hence, single use of either $Fe^{3+}$ or genipin is not able to meet the demand of rapid cross-linkable and long-term effectiveness under physiological conditions.

In one example, the gluing macromer and long-term acting crosslinker may be mixed together and stored in solid form, while the rapid crosslinker may be separately stored in solid form. For example, the solid mixture of gelatin-dopamine conjugates (or other gluing macromer) and genipin (or other long-term acting crosslinker) may be dissolved in normal saline solution; the concentration is 10%-50% (w/v, g/mL) and 2-40 mM for gelatin-dopamine conjugates (or other gluing macromer) and genipin (or other long-term acting crosslinker), respectively. The rapid crosslinkers containing multivalent metal ions (such as $Cu^{2+}$, $Zn^{2+}$, $Al^{3+}$, $Fe^{3+}$ and $Cr^{3+}$) may be dissolved in normal saline solution to get a 500 mM solution. The mixture solution of gelatin-dopamine conjugates and genipin may be smeared on tissue surface with a cotton bud, followed by the drip of the multivalent metal ion solution (final concentration is 5-50 mM) with a syringe on the tissue surface (coated with mixture solution of gelatin-dopamine conjugates and genipin), and then tissue surfaces may be adhered after gentle press for about 10 seconds.

In another example, the three components may be stored separately after dissolving in normal saline solution in the following composition: 10%-50% (g/mL) gluing macromer, 500 mM long-term acting crosslinker, 500 mM rapid crosslinkers. For example, genipin (or other long-term acting crosslinker) solution may be added into gelatin-dopamine conjugates (or other gluing macromer) solution with a syringe, resulting 2-40 mM genipin (or other long-term acting crosslinker) solution. This mixture solution may be smeared on tissue surface with a cotton bud, followed by the drip of the multivalent metal ion solution (final concentration is 5-50 mM) with a syringe on the tissue surface (coated with mixture solution of gelatin-dopamine conjugates and genipin), and then tissue surfaces may be be adhered after gentle press for about 10 seconds.

In a further example, a method for coating an anatomical site on tissue of a living organism using said tissue adhesive composition may include steps of applying to the site a) a mixture solution containing gluing macromer and long-lasting crosslinker; followed by b) dripping the rapid cross-linker on the site; and then c) applying gentle press on the site for approximately 10 seconds.

By designing and developing a double-cross-linked tissue adhesive disclosed herein, problems mentioned above may be addressed and the tissue adhesive is able to meet all requirements for in vivo applications such as seroma prevention.

Advantageously, the catechol-grafted macromer as the gluing backbone may be a natural or a synthetic bio/macromolecular which does not contain any toxic components, in particular, any aldehyde or cyan groups. The tissue adhesive is designed and fabricated using a novel double-crosslinking principle, where it integrates qualities of rapid crosslinking (by rapid ion-catechol complexation) and long-term effectiveness (by covalent crosslinking). The novel tissue adhesive does not possess acute or chronic toxicity, thereby rendering its suitability for use in in vivo applications, such as seroma prevention after mastectomy.

Example 1: Synthesis of Gelatin-Dopamine Gluing Macromer

Figure 2:
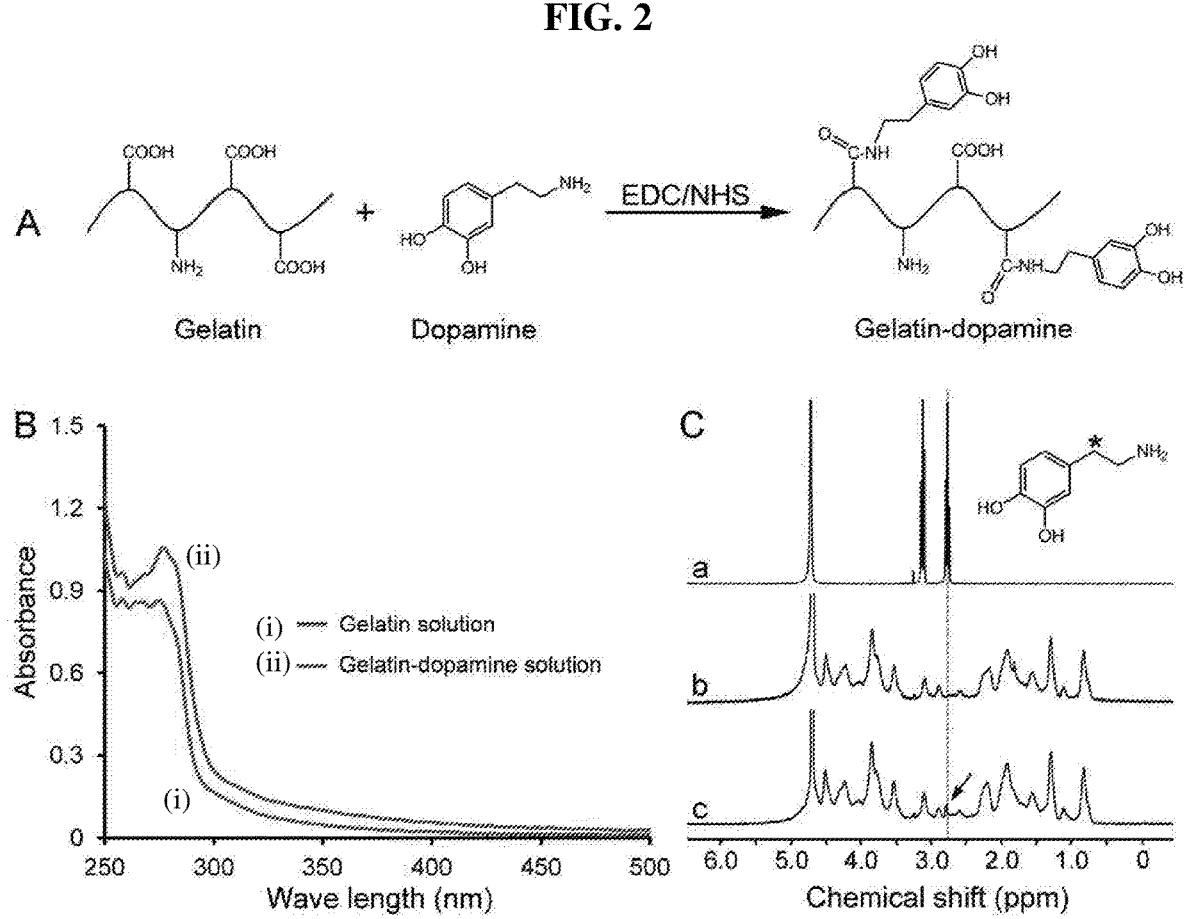
FIG. 2 shows (A) synthesis scheme of gelatin-dopamine conjugate; (B) UV-vis spectra of (i) gelatin solution (10%, g/mL), and (ii) gelatin-dopamine solution (10%, g/mL); and (C) $^1$H NMR spectra of (a) dopamine, (b) gelatin, and (c) gelatin-dopamine; the characteristic proton chemical shift of methylene groups (asterisk-marked) is shown by a vertical dashed-line through (a), (b), and (c) and an arrow at (c).

Gelatin-dopamine gluing macromer was synthesized by ethyl-dimethyl aminopropylcarbodiimide (EDC) and N-hydroxy-succinimide (NHS) coupling chemistry (FIG. 2(A)). Briefly, gelatin (2.0 g, Type A from porcine skin) was dissolved in 100 mL of phosphate buffered saline (PBS) at 60° C. EDC (0.5 g) and NHS (0.3 g) was added into the solution and pH value of the mix solution was adjusted to 6.0. After 30 minutes' stirring, 1.0 g of dopamine was added and the pH value of reaction solution was maintained from 5.0 to 6.0 for 24 hours at 37° C. After the reaction, the solution was dialyzed in acidified deionized water for one day and deionized water for 5 hours, and lyophilized. The resultant gelatin-dopamine conjugate was characterized with UV spectroscopy (FIG. 2(B)) and $^1H$ NMR spectroscopy (FIG. 2(C)). Content of catechol groups in the gelatin-dopamine conjugate was 3.7 μg/mg as determined using Arnow's method (Arnow, *J. Biol. Chem.* 1937, 118:531-537).

Example 2: Property of the Adhesive

Figure 4:
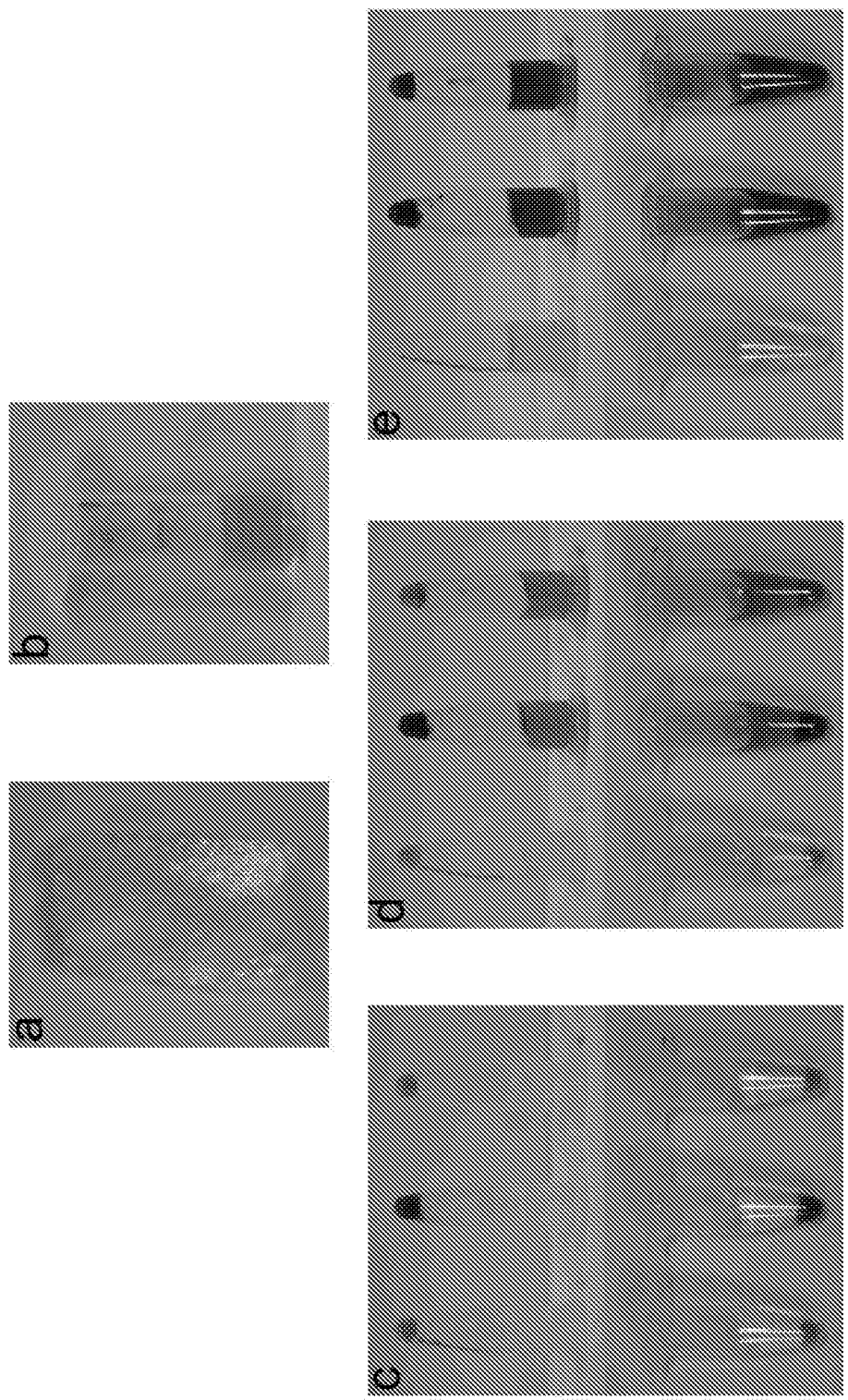
FIG. 4 shows photographs depicting property of the gelatin-dopamine gluing macromers, in (a) dry foam, and (b) viscous solution (15%, g/mL). Appearance changes of $Fe^{3+}$ single-cross-linked hydrogel without (left samples in (c), (d), and (e)) or with genipin (right samples in (c), (d), and (e)), and pre-fabricated double-cross-linked hydrogel (middle samples in (c), (d), and (e)) in simulated body fluid (SBF) containing 0.5% (v/v) fetal bovine serum after (c) 0 hours, (d) 3 hours, and (e) 24 hours incubation at 37° C. In (c), (d), and (e), the top row is the inverted tubes of the corresponding tubes in the bottom row.

Gross overview of the gelatin-dopamine gluing macromer is as shown in FIG. 4(a), which is not adhesive in its solid form. This gluing macromer may be dissolved in saline to form viscous solution as shown in FIG. 4(b). The long-acting cross-linker (such as genipin) can be added into the gluing macromer solution before use. The gelatin-dopamine gluing macromer can be rapidly (within seconds) cross-linked with $Fe^{3+}$ by forming $Fe^{3+}$-catechol complex, and also be covalently cross-linked with genipin (FIGS. 3(a) and (b)). After applying the mix solution on tissue surfaces, the catechol moieties in gluing macromers can bind to the surface, and then quickly cross-linked by catechol-$Fe^{3+}$ complexation on the addition of $FeCl_3$. This single cross-linked hydrogel is light yellow. The complexation-covalent double cross-linked tissue adhesive will be achieved after 2 hours at 37° C., meanwhile, the tissue adhesive become blue (FIG. 8A to D).

Example 3: Stability of $Fe^{3+}$ Single Cross-Linked Hydrogel

The gelatin-dopamine gluing macromer may be rapidly (within seconds) crosslinked with multivalent metal ions such as $Cu^{2+}$, $Zn^{2+}$, $Al^{3+}$ and $Fe^{3+}$ by forming ion-catechol complex, however, the ion-catechol complex was unstable in solution even containing trace protein based on studies conducted herein. The stability of $Fe^{3+}$-catechol complex was evaluated as follows.

The inventors studied the stability of the sticky hydrogel prepared with single catechol-$Fe^{3+}$ complexation cross-linking. 70 µL of gelatin-dopamine solution (15%, g/mL) was transferred into a mold. The gelatin-dopamine solution gelled quickly to form a sticky hydrogel within seconds after the addition of 10 µL of $FeCl_3$ solution. The sticky hydrogel was removed into a FBS solution (0.5%, g/mL). As shown in FIG. 4(c) to (e), the brown, single complexation cross-linked hydrogel was intact after 3 hours' immersion, yet broken down after 24 hours and the liquid became light yellow. This single $Fe^{3+}$ crosslinked adhesive has the virtue of rapid gelation, but cannot achieve long-term effectiveness.

By adding the long-acting (covalent) cross-linker such as genipin, which can cross-link the macromolecules containing primary amine groups, the inventors have shown that stability of the $Fe^{3+}$ single-cross-linked hydrogel is improved.

In other tests carried out, stability of the $Fe^{3+}$ single-cross-linked hydrogel (through $Fe^{3+}$-catechol complexation) and double-cross-linked hydrogel (through $Fe^{3+}$-catechol complexation and genipin-gluing macromer covalent cross-linking) in simulated body fluid (SBF) solution containing 0.5% (v/v) fetal bovine serum (FBS, PAA Laboratories) were investigated. At the same time, the covalent cross-linking of gelatin-dopamine by genipin was investigated in the SBF solution.

Briefly, 50 µL of gluing macromer solution in a 1.5 ml centrifuge tube, and $Fe^{3+}$ single-cross-linked sticky hydrogel was rapidly formed after adding 5 µL of 100 mM $FeCl_3$ solution. For the fabrication of double-cross-linked hydrogel, the genipin solution (10%, g/mL) was first added into gluing macromer solution to make a mixture solution containing 0.5% (g/mL) genipin. The mixture solution (50 µL) was transferred into a 1.5 ml centrifuge tube, followed by adding 5 µL, of $FeCl_3$ solution (100 mM). The sticky hydrogel containing genipin was placed in a humidified incubator at 37° C. for 2 hours. The blue pigments could be observed when the gluing macromer was covalent cross-linked with genipin.

The gelation time of gelatin solution in the presence of genipin was about two hours; this time may be shortened to 35 minutes by optimizing conditions, such as adding aided crosslinkers, for example, polylysine, and adjusting concentration of genipin. This shortened time was, however, still too long to serve as a suitable tissue adhesive in clinical applications. Although such cross-linking reaction was time-consuming, the covalent crosslinked adhesive generated was stable and may provide long-term effectiveness in physiological environments.

Besides, to evaluate the formation of the covalent cross-linking in $Fe^{3+}$ single-cross-linked hydrogel, the $Fe^{3+}$ single-cross-linked hydrogel was fabricated with 50 µL, of gluing macromer solution (15%, g/mL) containing genipin (0.5%, g/mL) in a 1.5 ml centrifuge tube. Subsequently, 0.8 mL of simulated body fluid (SBF) supplemented with 0.5% (v/v) fetal bovine serum (FBS, PAA Laboratories) was added into the three tubes, and incubated at 37° C. The appearance changes in the $Fe^{3+}$ single-cross-linked hydrogel with or without genipin, and double-cross-linked hydrogel, as well as the color of the SBF solution were observed as a function of incubation time, and shown in FIGS. 4(c), (d), and (e).

As seen in FIGS. 4(c), (d), and (e), the $Fe^{3+}$ single-cross-linked and double-cross-linked hydrogel is brown and dark blue, respectively, and the SBF solution is nearly colorless. After 3 hours' immersion, the single-cross-linked hydrogel was intact, whereas, whose color became lighter. Meanwhile, the medium changed into very light brown. The double-cross-linked hydrogel developed to deep dark blue, at the same time, the SDF solution turned into blue. Interestingly, the thin blue pigments were observed on the surface of $Fe^{3+}$ single-cross-linked hydrogel and SBF solution, moreover the SDF solution also became blue. After 24 hours' incubation, the $Fe^{3+}$ single-cross-linked hydrogel without genipin completely dissolved, however, the $Fe^{3+}$ single-cross-linked hydrogel with genipin kept intact and fully graded from brown to dark blue. The color of SDF solution became deeper compared with the corresponding samples by 3 hours' immersion. These results indicated that the $Fe^{3+}$ single-cross-linked tissue adhesive has the virtue of rapid gelation but cannot achieve long-term effectiveness in vivo; however, significantly, the double-cross-linked tissue adhesive not only be gradually formed even immersed in SDF solution, but also kept stable under in vivo conditions.

Example 4: Cytocompatibility of the Double-Cross-Linked Tissue Adhesive

Cytocompatibility of the double-cross-linked tissue adhesive was studied in detail, using porcine chondrocytes (PCCs) and human dermal fibroblasts (HDFs) as model cell, respectively.

First, the cytotoxicity of the extract solutions of this double-cross-linked tissue adhesive was evaluated by using the extract solutions of bovine serum albumin-glutaraldehyde tissue adhesive (named as BioGlue) and pure culture medium without any extract solution (named as pure medium) as positive and negative controls, respectively.

Briefly, the double-cross-linked tissue adhesive was prepared from 1.0 mL of gluing macromer solution in each 15 mL centrifuge tube. Similarly, the bovine serum albumin-glutaraldehyde tissue adhesive was synthesized from 0.8 mL of bovine serum albumin solution (45%, g/mL) and 0.2 mL of glutaraldehyde solution (10%, v/v) according to the reported method. 5 mL of culture medium for PCCs and HDFs culture was filled into the tubes, respectively, and kept in 4° C. for seven days. These extract solutions were filtered through a 0.22 µm filters, respectively. The extract solution of the double-cross-linked tissue adhesive was diluted with corresponding culture medium to make the dilutions contain the initial extract solution of 100%, 50%, and 25% volume percentage and named as Extract 100, Extract 50, and Extract 25, respectively.

The PCCs and HDFs were seeded in the 96-well plate at a density of $3\times10^3$ cells per well respectively, and cultured for 24 hours in 200 µL of corresponding pure culture medium. Thereafter, the culture medium was replaced with the extract solution dilutions and control solutions, respectively, and which were changed every other day. At predetermined time points, the MTT assay was carried out. Briefly, the culture solutions were replaced with a mix solution of 180 µL of fresh DMEM and 20 µL of 5 mg/mL MTT (3-(4,5-dimethylthiazol-2-yl)-2,5-diphenyl tetrazolium bromide). The plate was incubated at 37° C. for 4 hours, the medium was removed, and 200 µL, of DMSO was added to dissolve the formazan crystals. The optical density (OD) values were measured at the wavelength of 570 nm using a microplate reader.

Figure 5:
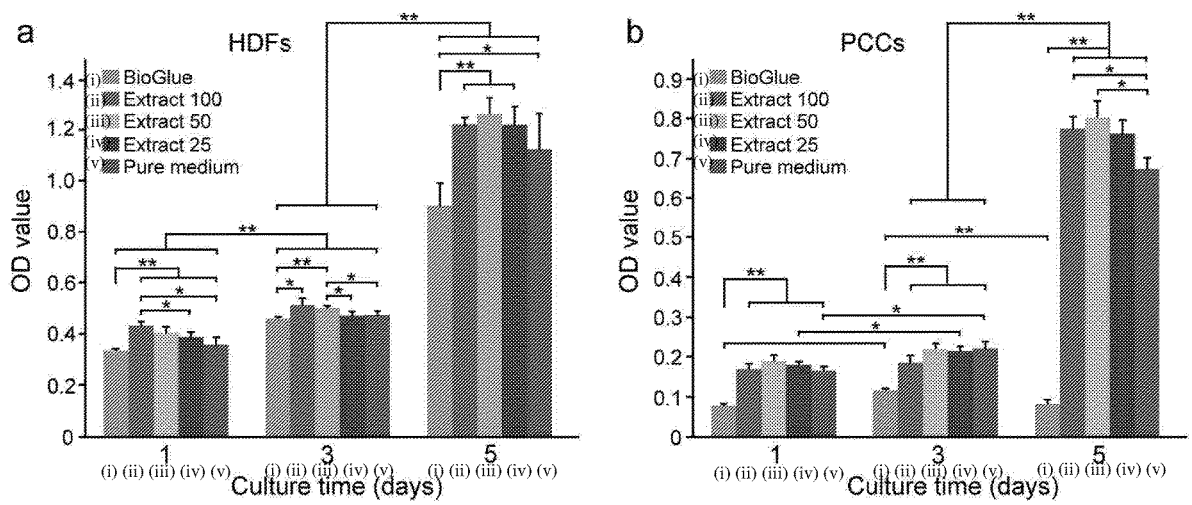
FIG. 5 shows graphs showing cell growth with culture solutions containing 100% (Extract 100, (ii)), 50% (Extract 50, (iii)), and 25% (Extract 25, (iv)) of initial extract solution, respectively, and the extract solution of bovine serum albumin-glutaraldehyde tissue adhesive (BioGlue, positive control, (i)) and pure culture medium without any extract solution (Pure medium, negative control, (v)), for (a) HDFs (human dermal fibroblasts) and (b) PCCs (porcine chondrocytes).

As shown from the OD value in FIG. 5(a), all the HDFs showed significant proliferation from day 1 to 3 and 5. However, the HDFs cultured with the 100% initial extract solution (Extract 100) exhibited higher cell viability than those cultured with BioGlue and Pure medium at each time points. Surprisingly, the cell viability of HDFs cultured in solutions containing extract solution of double-cross-linked tissue adhesive showed a decreasing trend along with the decrease of the initial extract solution' content.

Referring to FIG. 5(b), the cell viability of PCCs cultured with Extract 100, 50, and 25 showed increasing trend from day 1 to 3 and was significantly increased from day 3 to 5, as well as which was significantly higher than that of PCCs cultured with BioGlue at any time points. Furthermore, the cell viability of PCCs cultured with Extract 100, 50, and 25 was significantly higher than that of PCCs cultured with Pure medium on day 5. These results indicate the extract solution of this double-cross-linked tissue adhesive not inhibits cell growth, can even enhance the cell proliferation.

To further assess cytocompatibility of the double-cross-linked tissue adhesive, cell adhesion and proliferation on fresh prepared double-cross-linked tissue adhesive was studied by the monolayer culture of HDFs. Briefly, the double-cross-linked tissue adhesive was fabricated from 40 μL of gluing macromer solution in a 96-well plate. Cell suspensions were seeded on top of the double-cross-linked tissue adhesive at a density of 3×10³ cells/well, and incubated at 37° C. in 5% $CO_2$ atmosphere. Cell proliferation was determined with MTT assay as mentioned above. Pictures were taken under microscope after one day of culture.

Figure 6:
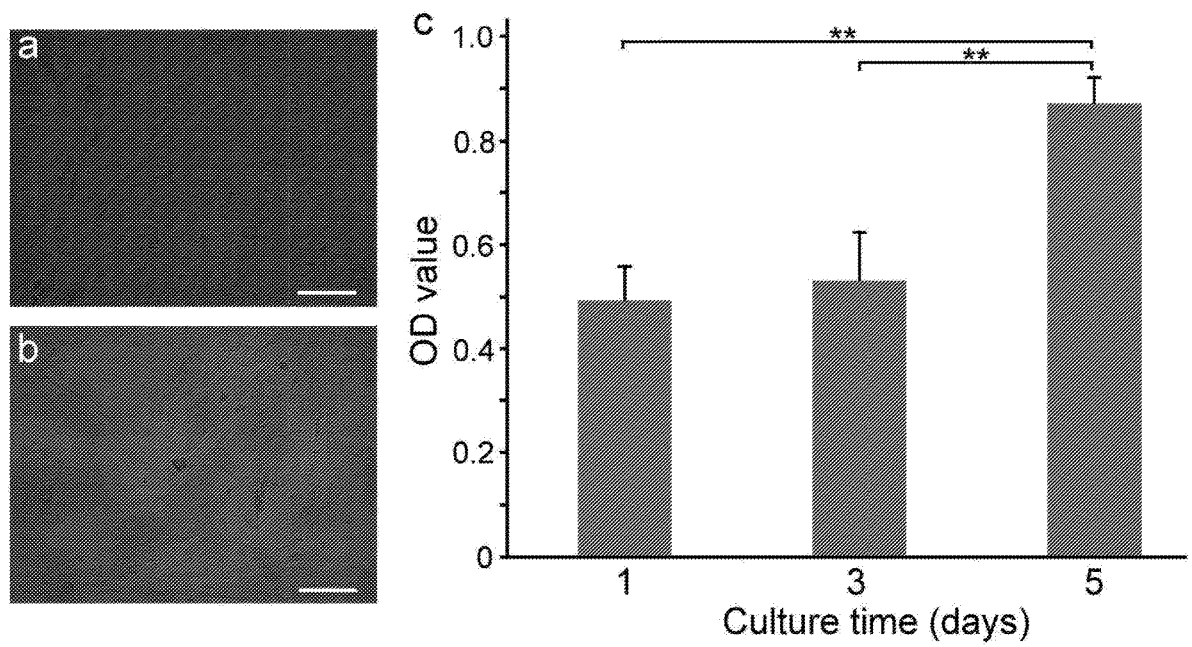
FIG. 6 shows phase contrast image of adhered HDFs on (a) tissue culture plastic (TCP), and (b) double-cross-linked tissue adhesive. (c) is a graph depicting proliferation of HDFs on double-cross-linked tissue adhesive.

As shown in FIG. 6(b), the fibroblasts showed comparable adhesion and spreading on the double-cross-linked tissue adhesive to those on tissue culture plastic (TCP) (FIG. 6(a)). Moreover, cell viability of HDFs statistically increased after five days' culture (FIG. 6(c)), proved by the increase of OD value. These results further demonstrated the cytocompatibility of this double-cross-linked tissue adhesive.

Hemocompatibility of this double-cross-linked tissue adhesive was evaluated in vitro. Briefly, approximately 5 ml whole blood was drawn from healthy volunteers into the syringe preloaded with heparin sodium. The double-cross-linked tissue adhesive synthesized from 200 μL of gluing macromer solution in cylindrical molds (diameter 6.5 mm) and aforementioned extract solution of double-cross-linked tissue adhesive (200 μL) was transferred into 4 mL of 0.9% sodium chloride (NaCl) in each 15 mL centrifuge tube, respectively. 200 μL of whole blood was added to each tube, and which was incubated for 60 minutes at 37° C. Positive and negative controls were produced by adding 0.2 ml of whole blood into 4 mL of DI water and 0.9% NaCl, respectively. The samples were centrifuged at 1500 rpm for 5 minutes. The OD value of the supernatant was measured at the wavelength of 545 nm using a microplate reader. The hemolysis was calculated as follows:

Hemolysis (%)=(OD of sample−OD (−) control)/ (OD (+) control−OD (−) control)×100%

TABLE 3

Hemolysis of blood erythrocyte

| Sample | OD value | Hemolysis (%) |
|---|---|---|
| 0.9% NaCl | 0.136 ± 0.002 | −ve control |
| Water | 1.341 ± 0.011 | +ve control |
| Tissue adhesive | 0.142 ± 0.003 | 0.498 ± 0.273 |
| Extract solution | 0.144 ± 0.003 | 0.677 ± 0.292 |

As shown in TABLE 3, hemolysis was less than 1% for both fresh prepared double-cross-linked tissue adhesive and its extract solution, which is well within the permissible limit of 5% for biomaterials, indicating the hemocompatibility of this double-cross-linked tissue adhesive.

The viscoelastic properties of gluing macromer (gelatin-dopamine) solution, $Fe^{3+}$ single-cross-linked hydrogel, and double cross-linked tissue adhesive were determined by using a rheometer (TA Instruments, Model AR2000ex) equipped with 20 mm diameter stainless steel parallel plate geometry. The double-cross-linked adhesive samples were fresh prepared before rheological tests. For $Fe^{3+}$ single-cross-linked hydrogel (named as gelatin-dopamine+$Fe^{3+}$), the data were recorded as soon as the addition of $FeCl_3$ solution. The operation temperature was maintained at 37° C.

To ensure the rheological measurements within a linear viscoelastic range, the dynamic strain sweep was conducted prior to the frequency sweep, and the strain was determined to be 5%. Elastic modulus (G') and viscous modulus (G") was measured by performing frequency sweeps between 0.01 and 1.0 Hz.

Figure 7:
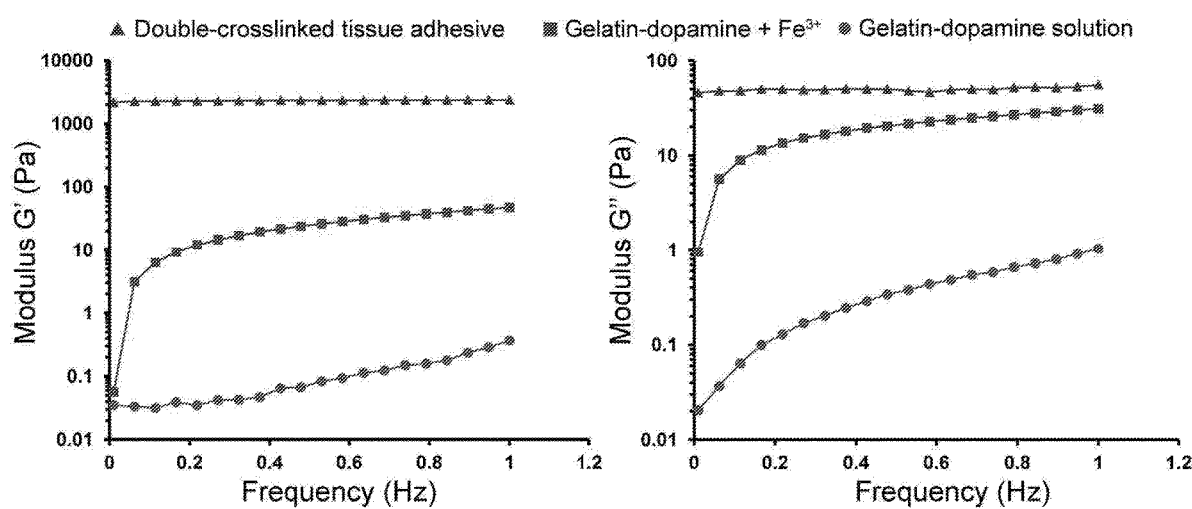
FIG. 7 shows graphs of elastic modulus (G') and viscous modulus (G") as a function of frequency (hertz) for double-cross-linked tissue adhesive, $Fe^{3+}$ single-cross-linked hydrogel (gelatin-dopamine+$Fe^{3+}$), and the gluing macromer (gelatin-dopamine) solution.
Figure 8:
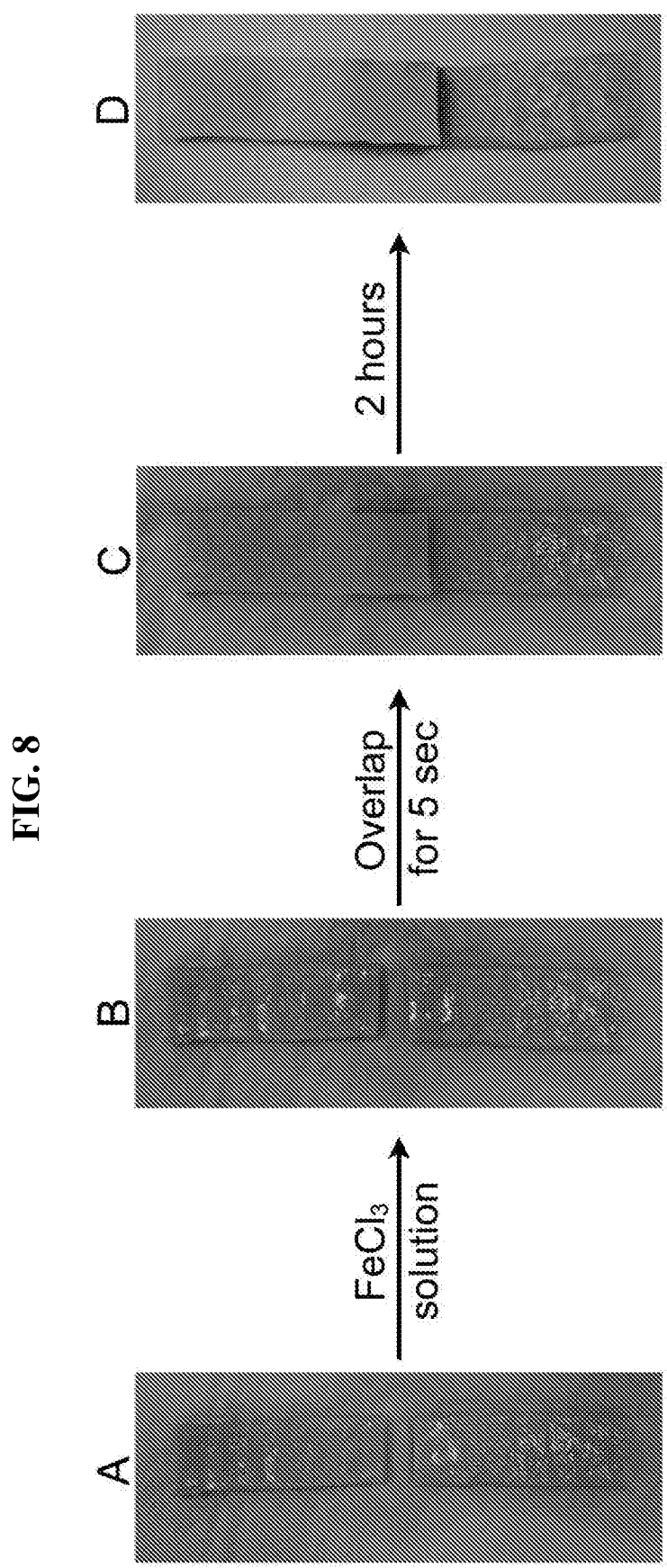
FIG. 8 is a schematic illustration of operation process of this double-cross-linked tissue adhesive according to an embodiment, where (A) mixture solution of gelatin-dopamine gluing macromer (15%, g/mL) and genipin (0.5%, g/mL) is applied on tissue surfaces; (B) drops of $FeCl_3$ solution (100 mM) are added on working area, rapidly forming sticky hydrogel; (C) working areas of the two porcine skins are overlapped and surfaces of both tissues are adhered after gentle press for about 5-10 seconds; (D) complexation-covalent double cross-linked tissue adhesive is achieved after 2 hours at 37° C., whereby the tissue adhesive become blue at that moment.

As seen in FIG. 7, the rapid increase of G' and G" for the specimen of "gelatin-dopamine+$Fe^{3+}$" indicated the gluing macromer could be cross-linked with $Fe^{3+}$ within seconds. Moreover, the G' and G" further increased when the gluing macromer was covalently cross-linked with genipin.

Example 5: Adhesion Test

The adhesion force was determined by lap shear strength test, using an Instron mechanical tester (Model 5543) equipped with a 100 N load cell.

Considering the biological similarity to human dermis, fresh porcine skin was used as an adherend without any purification to mimic clinical condition. The typical operation process was shown in FIG. 8. The adhesion tests were performed at a tensile rate of 1.0 mm/min, as shown in FIG. 9(b), and the adhesion (shear) strength was calculated by dividing the maximum load by the overlapping area.

The adhesion tests for this double-cross-linked tissue adhesive were carried out under different conditions. Briefly, the gluing macromer solution (15%, g/mL) containing genipin (0.5%, g/mL) was applied to the fat layer (inside) of each wet porcine skin, followed by adding drops of $FeCl_3$ solution (100 mM). The working areas were gently pressed together with fingers for about 5 seconds. Subsequently, the adhesion tests were performed to get the adhesion strength that was named as "rapid gluing" strength. The samples prepared with above-mentioned method were placed in a humidified incubator at 37° C. for 2 hours to complete the second cross-linking of gluing macromer with genipin, and then the adhesion tests were carried out to get the "double-cross-link gluing" strength. The samples after double-cross-linking were immersed in SBF containing 0.5% (v/v) FBS for 24 hours on a rotary shaker (80 rpm), and the adhesion tests were performed to get the adhesion strength named as "long-term gluing" strength. In addition, the collagen layer (outside) of porcine skin and fresh porcine articular cartilage were glued with double-cross-linked tissue adhesive, the adhesion tests were carried out, and the adhesion strength was named as "collagen layer gluing" and "cartilage gluing" strength, respectively.

TABLE 4

Adhesion strength of the tissue adhesive under different conditions

| Adhesion pattern | Adhesion strength (kPa) | Adhesion strength of Fibrin glue (kPa) |
| --- | --- | --- |
| Rapid gluing | 9.3 ± 4.9 | |
| Double-cross-link gluing | 24.7 ± 3.3 | 17.6 |
| Long-term gluing | 12.9 ± 0.5 | |
| Collagen layer gluing | 20.4 ± 4.0 | |
| Cartilage gluing | 194.4 ± 20.7 | Less than 8.0 |

Figure 9:
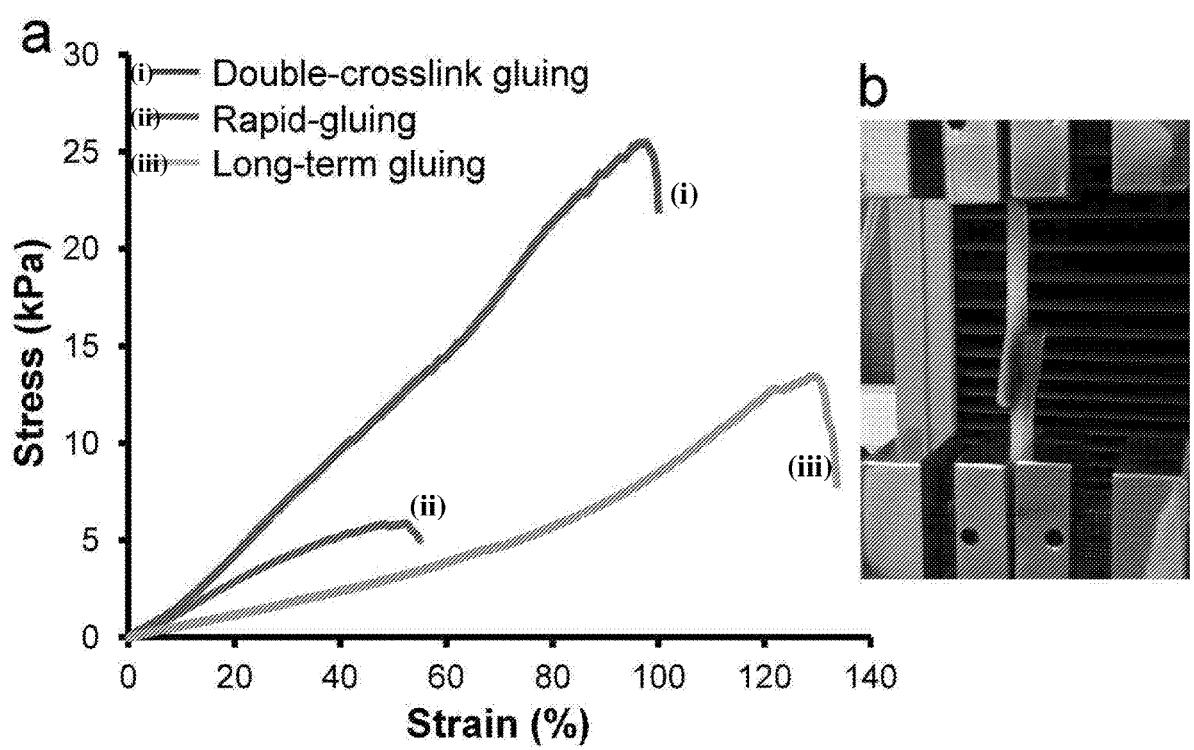
FIG. 9 depicts (a) representative stress-strain curves of the tissue adhesive under different conditions of (i) double-cross-link gluing, (ii) rapid gluing, and (iii) long-term gluing; and (b) representative image of lap shear strength test.
Figure 10:
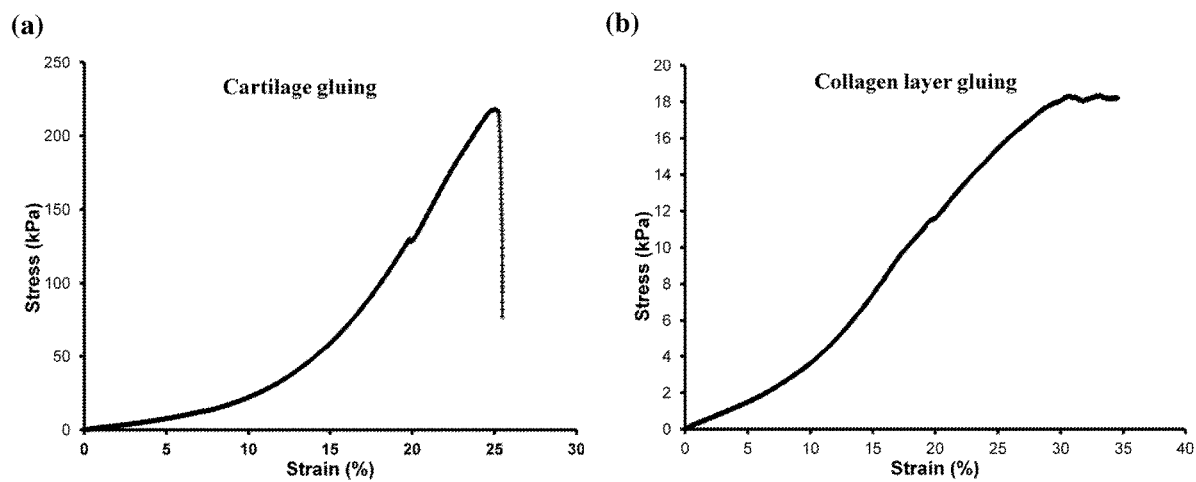
FIG. 10 are graphs showing representative stress-strain curves of the adhesives after (a) cartilage gluing, and (b) collagen layer (of porcine skin) gluing.

As shown in TABLE 4, FIG. 9, and FIG. 10, the inventors have performed the adhesion tests of this double-cross-linked tissue adhesive in detail. The tissue adhesive exhibited sufficient adhesion strength for seroma prevention and many other in vivo applications.

Example 6: Degradation Test

The degradation of the double-cross-linked tissue adhesive was first investigated in vitro. Briefly, as-synthesized double-cross-linked tissue adhesive samples from 150 μL gluing macromer solution in cylindrical molds (diameter 6.5 mm) were weighed ($W_0$). Twenty samples were placed into a 50 mL centrifuge tube containing 10 mL of trypsin-EDTA solution (25200, Life Technologies) that was diluted one fold with DMEM (Gibco), and incubated at 37° C. on a rotary shaker (150 rpm). At a predetermined time point, three samples were taken out and weighed ($W_t$) after wiping off the solution on the surfaces. The remaining weight fraction of the tissue adhesive was determined as follows:

Remaining weight (%)=$W_t/W_0 \times 100\%$

Figure 11:
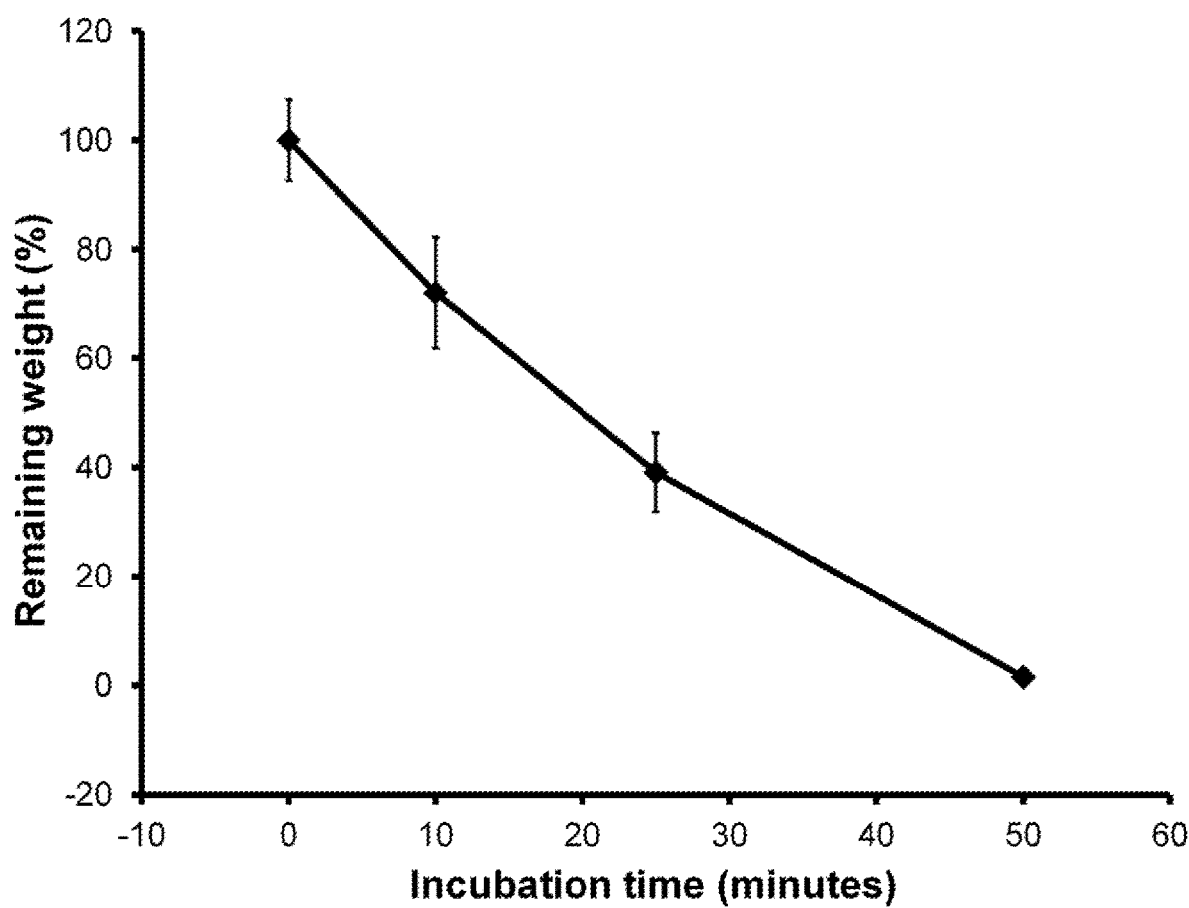
FIG. 11 is a graph showing degradation of the double-cross-linked tissue adhesive as a function of incubation time in trypsin-ethylenediaminetetraacetic acid (EDTA) solution.

As shown in FIG. 11, the double-cross-linked tissue adhesive exhibits degradation capacity in trypsin solution.

The in vivo biocompatibility and degradability of the double-cross-linked tissue adhesive was examined. All animal experiments were performed under guidelines approved by the Institutional Animal Care and Use Committees, SingHealth, Singapore. The fresh fabricated double-cross-linked tissue adhesives from 60 μL of above-mentioned gluing macromer solution in cylindrical molds (diameter 5 mm) were implanted subcutaneously into NCr nude mice. Each animal received four samples and one animal was sacrificed per time point. The samples were carefully dissected from surrounding tissue, dried, and weighed. The weights of samples on day 4 were defined as the initial weight ($W_0$), and the samples on day 14 and 28 were weighed ($W_t$). The remaining weight fraction of the tissue adhesive was calculated as: remaining weight (%)=$W_t/W_0 \times 100\%$. For histological evaluation, the samples surrounded with tissue were fixed in 4% paraformaldehyde for 3 days at 4° C., embedded in paraffin. Sections (thickness 6 μm) were stained using hematoxylin and eosin (H&E) to analyze the degree of inflammation and fibrosis.

Figure 12:
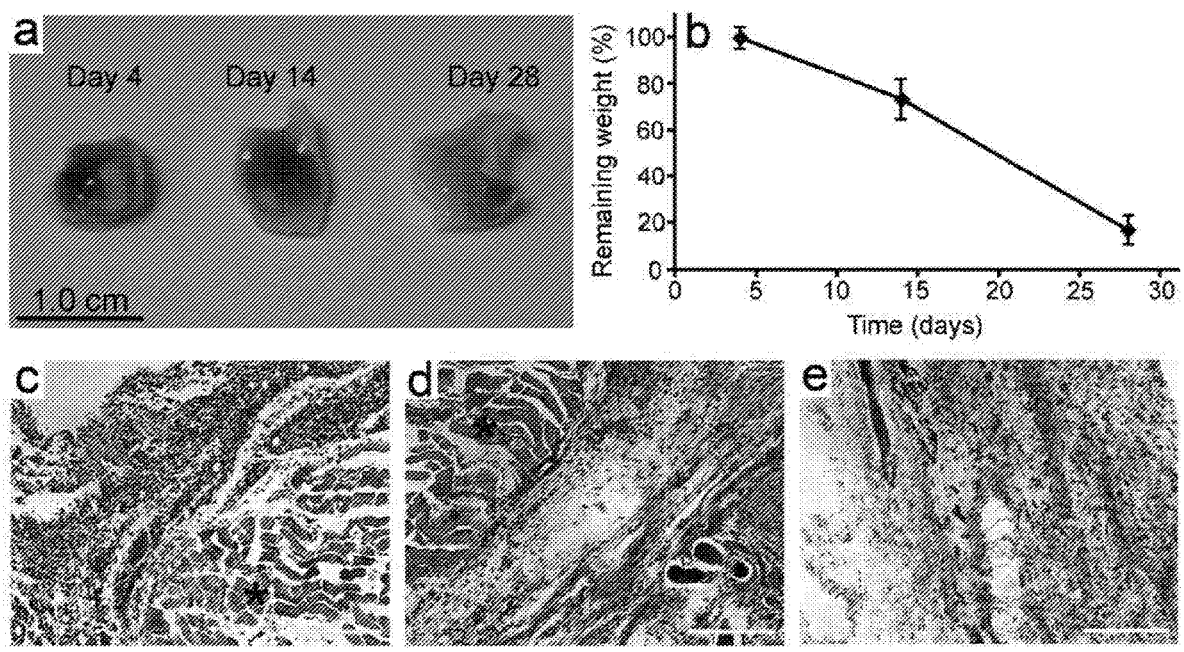
FIG. 12 shows (a) gross view of the samples (containing murine skins) extracted on day 4, 14, and 28, respectively, after implantation of the double-cross-linked tissue adhesive in nude mice; (b) degradation of the adhesives in vivo; (c) to (e) H & E staining of tissue sections immediately adjacent to the tissue adhesive after (c) 4, (d) 14, and (e) 28 days' implantation, where the adhesives are marked with a star. Scale bar in (c), (d) and (e) denote 100 µm.

As shown in FIGS. 12(a) and (b), the tissue adhesive also gradually degraded in vivo, and a mild inflammation was observed on day 4 and 14 after implantation, however, these tissue responses were not detected on day 28. Besides, collagen deposition was not observed across the 28 days' implantation.

A kit for adhering biological tissues according to various embodiments may include three components: catechol-grafted gluing macromer solution, rapid crosslinker solution, and long-acting crosslinker solution. The tissue adhesive disclosed herein is very easy to use. For example, a user may first add the long-acting crosslinker solution into the gluing macromer solution, and the mixture may be applied on a first tissue surface. This may be followed by addition of the rapid crosslinker on the mixture. Adhesion of a second tissue to the first tissue may be carried out by contacting the first tissue with the second tissue at the region where the biological tissue adhesive is applied, and exerting gentle pressure on one or both the first and second tissues.

In summary, the inventors have synthesized gelatin-dopamine gluing macromer containing catechol groups, by EDC/NHS coupling chemistry, and successfully developed complexation-covalent double cross-linked tissue adhesive with both rapid cross-linker $Fe^{3+}$ and long-term acting cross-linker genipin. $Fe^{3+}$ and genipin plays respective role in the adhesion process of this novel tissue adhesive. $Fe^{3+}$ can rapidly cross-link the gelatin-dopamine gluing macromer within seconds and stable for several hours; at the same time, the covalent cross-linking of gelatine-dopamine with genipin is taking place, which needs about two hours. Although the gelation time of gelatin solution in the presence of genipin may be shortened to 35 minutes by optimizing conditions such as adding aided crosslinkers (such as polylysine) and adjusting the concentration of genipin, it is still too long to serve as an available tissue adhesive in clinical applications. Although this cross-linking reaction is time-consuming, the resultant covalent crosslinking is stable and long-term effective in physiological environments.

The novel double-cross-linked tissue adhesive disclosed herein combines the qualities of $Fe^{3+}$-catechol complexation cross-linking (fast and strong wet adhesion) and covalent cross-linking (stable). Process to prepare the tissue adhesive may be scaled up easily, hence it may be commercialized without major modification. The cytocompatibility and adhesion strength were evaluated, and the results obtained from in vitro experiments suggested that the biological tissue adhesive disclosed herein is a promising tissue adhesive in clinical applications, in particular for in vivo applications as demonstrated by rat mastectomy seroma model.

There are several advantages in the novel tissue adhesive disclosed herein. Firstly, the preparation cost is inexpensive and feasible for scaling up. Raw materials such as gelatin and chitosan are in abundance and cheap. Catechol-grafted gluing macromer, for example, may be achieved in a single step reaction without using special processing conditions such as high temperature, high vacuum, high pressure, and/or specific catalyst, and special equipment. Secondly, use of the tissue adhesive is very easy and convenient, rendering its feasibility for clinical applications. Generally, long-acting crosslinkers such as genipin may be added into catechol-grafted gluing macromer solution, and the mix solution may be applied on surface of a tissue. Solutions containing multivalent ions such as $FeCl_3$ and $ZnCl_2$ may be dripped on each surface, and pressed gently for about 10 seconds.

Thirdly, the tissue adhesive disclosed herein exhibited relatively high adhesive force and is cytocompatible according to the results obtained in vitro. Fourthly, the tissue adhesive is non-toxic, easy to store and transport. For example, catechol-grafted macromolecule, rapid crosslinker, and long-acting crosslinker of the tissue adhesive are not contraband goods, are non-toxic, and may be stored at −4° C. for several months.

Tissue adhesive disclosed herein may be adopted by medical materials corporations, and the end user may be a surgeon. The tissue adhesive may be commercialized and used clinically for in vivo applications such as semora prevention after surgery, for example mastectomy and lymph node dissections, so as to allow better and faster recovery of patients.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A biological tissue adhesive composition comprising
   (i) a gluing macromer comprising one or more macromolecules (a) grafted with a catechol-containing compound comprising at least one catechol moiety and (b) comprising at least one cross-linkable functional group, wherein the catechol-containing compound is selected from the group consisting of dopamine, hydrocaffeic acid, dihydroxyphenylalanine, 3,4-dihydroxylhydrocinnamic acid, and combinations thereof, and wherein amount of catechol moiety in the one or more macromolecules grafted with the catechol-containing compound is in the range of 5% (w/w) to 20% (w/w);
   (ii) a first cross-linker for cross-linking the at least one catechol moiety, wherein the first cross-linker comprises a multivalent metal ion; and
   (iii) a second cross-linker selected from the group consisting of genipin, polygenipin, genipin-grafted molecule, and combinations thereof for covalently cross-linking the at least one cross-linkable functional group, wherein the one or more macromolecules are cross-linked by (a) complex formation between the at least one catechol moiety and the multivalent metal ion, and (b) covalent bonding of the at least one cross-linkable functional group with the second cross-linker.

2. The biological tissue adhesive composition according to claim 1, wherein the one or more macromolecules does not contain an aldehyde group and/or a cyan group.

3. The biological tissue adhesive composition according to claim 1, wherein the one or more macromolecules is selected from the group consisting of an amino group functionalized polysaccharide, a polyamino acid, and combinations thereof.

4. The biological tissue adhesive composition according to claim 1, wherein the one or more macromolecules is selected from the group consisting of gelatin, bovine serum albumin (BSA), chitosan, polyethylenimine, hyaluronan, dextran, poly(asparagic acid), poly(glutamic acid), chondroitin sulfate, and combinations thereof.

5. The biological tissue adhesive composition according to claim 1, wherein the one or more macromolecules comprises a natural macromer.

6. The biological tissue adhesive composition according to claim 1, wherein the multivalent metal ion is selected from the group consisting of $Cu^{2+}$, $Zn^{2+}$, $Al^{3+}$, $Fe^{3+}$, $Cr^{3+}$, and combinations thereof.

7. The biological tissue adhesive composition according to claim 1, wherein the second cross-linker comprises a macromolecule grafted with at least one α, β-unsaturated carbonyl or α, β-unsaturated sulfonyl group.

8. The biological tissue adhesive composition according to claim 1, wherein the one or more macromolecules has a number average molecular weight in the range of about 10,000 g/mol to about 100,000 g/mol.

9. A method of preparing a biological tissue adhesive composition according to claim 1, the method comprising
   a) providing a mixture of a gluing macromer comprising one or more macromolecules (a) grafted with a catechol-containing compound comprising at least one catechol moiety and (b) comprising at least one cross-linkable functional group, and a second cross-linker selected from the group consisting of genipin, polygenipin, genipin-grafted molecule, and combinations thereof, for covalently cross-linking the at least one cross-linkable functional group, wherein the catechol-containing compound is selected from the group consisting of dopamine, hydrocaffeic acid, dihydroxyphenylalanine, 3,4-dihydroxylhydrocinnamic acid, and combinations thereof, and wherein amount of catechol moiety in the one or more macromolecules grafted with the catechol-containing compound is in the range of 5% (w/w) to 20% (w/w); and
   b) adding a first cross-linker for cross-linking the at least one catechol moiety, wherein the first cross-linker comprises a multivalent metal ion, to the mixture so as to cross-link the one or more macromolecules by complex formation between the at least one catechol moiety and the multivalent metal ion.

10. The method according to claim 9, wherein the one or more macromolecules does not contain an aldehyde group and/or a cyan group.

11. The method according to claim 9, wherein the one or more macromolecules is selected from the group consisting of an amino group functionalized polysaccharide, a polyamino acid, and combinations thereof.

12. The method according to claim 9, wherein the one or more macromolecules are selected from the group consisting of gelatin, bovine serum albumin (BSA), chitosan, polyethylenimine, hyaluronan, dextran, poly(asparagic acid), poly(glutamic acid), chondroitin sulfate, and combinations thereof.

13. The method according to claim 9, wherein the one or more macromolecules comprises a natural macromer.

14. The method according to claim 9, wherein the second cross-linker comprises a macromolecule grafted with at least one α, β-unsaturated carbonyl group or α, β-unsaturated sulfonyl group.

15. The method according to claim 9, wherein the multivalent metal ion is selected from the group consisting of $Cu^{2+}$, $Zn^{2+}$, $Al^{3+}$, $Fe^{3+}$, $Cr^{3+}$, and combinations thereof.

16. The method according to claim 9, wherein the one or more macromolecules are cross-linked by complex formation between the at least one catechol moiety and the multivalent metal ion present in the first cross-linker before being cross-linked by covalent bonding between the at least one cross-linkable functional group and the second cross-linker.

17. A method of adhering biological tissues with a biological tissue adhesive composition according to claim 1, the method comprising
   a) applying a mixture of a gluing macromer comprising one or more macromolecules (a) grafted with a catechol-containing compound comprising at least one catechol moiety and (b) comprising at least one cross-linkable functional group, and a second cross-linker selected from the group consisting of genipin, polygenipin, genipin-grafted molecule, and combinations thereof, for covalently cross-linking the at least one cross-linkable functional group on a first biological tissue to form a coating, wherein the catechol-containing compound is selected from the group consisting of dopamine, hydrocaffeic acid, dihydroxyphenylalanine, 3,4-dihydroxylhydrocinnamic acid, and combinations thereof, and wherein amount of catechol moiety in the one or more macromolecules grafted with the catechol-containing compound is in the range of 5% (w/w) to 20% (w/w);
b) adding a first cross-linker for cross-linking the at least one catechol moiety, the first cross-linker comprising a multivalent metal ion, to the coating;
c) contacting a second biological tissue with the resultant coating; and
d) applying pressure to one or both the first biological tissue and the second biological tissue to adhere the first biological tissue to the second biological tissue.

18. The method according to claim 17, wherein the one or more macromolecules are cross-linked by complex formation between the at least one catechol moiety and the multivalent metal ion present in the first cross-linker before being cross-linked by covalent bonding between the at least one cross-linkable functional group and the second cross-linker.

* * * * *